United States Patent [19]
Prammer

[11] Patent Number: 6,005,389
[45] Date of Patent: Dec. 21, 1999

[54] PULSE SEQUENCES AND INTERPRETATION TECHNIQUES FOR NMR MEASUREMENTS

[75] Inventor: Manfred G. Prammer, Downingtown, Pa.

[73] Assignee: Numar Corporation, Malvern, Pa.

[21] Appl. No.: 08/816,395

[22] Filed: Mar. 13, 1997

Related U.S. Application Data

[60] Provisional application No. 60/013,484, Mar. 15, 1996.

[51] Int. Cl.[6] .................................................. G01V 3/00
[52] U.S. Cl. ........................................ 324/303; 324/300
[58] Field of Search ..................................... 324/303, 300, 324/312, 314, 307, 309; 73/152.06, 152.08

[56] References Cited

U.S. PATENT DOCUMENTS

| | | | |
|---|---|---|---|
| 3,508,438 | 4/1970 | Alger et al. | 73/152 |
| 4,710,713 | 12/1987 | Taicher et al. | 324/303 |
| 4,717,876 | 1/1988 | Masi et al. | 324/303 |
| 4,717,877 | 1/1988 | Taicher et al. | 324/303 |
| 4,717,878 | 1/1988 | Taicher et al. | 324/303 |
| 4,728,892 | 3/1988 | Vinegar et al. | 324/309 |
| 4,933,638 | 6/1990 | Kenyon et al. | 324/303 |
| 5,023,551 | 6/1991 | Kleinberg et al. | 324/303 |
| 5,212,447 | 5/1993 | Paltiel | 324/300 |
| 5,280,243 | 1/1994 | Miller | 324/303 |
| 5,309,098 | 5/1994 | Coates et al. | 324/303 |
| 5,349,184 | 9/1994 | Wraight | 250/266 |
| 5,350,925 | 9/1994 | Watson | 250/269.3 |
| 5,363,041 | 11/1994 | Sezginer | 324/303 |
| 5,376,884 | 12/1994 | Sezginer | 324/303 |
| 5,379,216 | 1/1995 | Head | 364/422 |
| 5,381,092 | 1/1995 | Freedman | 324/303 |
| 5,387,865 | 2/1995 | Jerosch-Herold et al. | 324/303 |
| 5,389,877 | 2/1995 | Sezginer et al. | 324/303 |
| 5,412,320 | 5/1995 | Coates | 324/303 |
| 5,432,446 | 7/1995 | Macinnis et al. | 324/303 |
| 5,486,761 | 1/1996 | Sezginer | 324/303 |
| 5,486,762 | 1/1996 | Freedman et al. | 324/303 |
| 5,497,087 | 3/1996 | Vinegar et al. | 324/303 |
| 5,498,960 | 3/1996 | Vinegar et al. | 324/303 |
| 5,517,115 | 5/1996 | Prammer | 324/303 |
| 5,557,200 | 9/1996 | Coates | 324/303 |
| 5,557,201 | 9/1996 | Kleinberg et al. | 324/303 |
| 5,565,775 | 10/1996 | Stallmach et al. | 324/303 |
| 5,680,043 | 10/1997 | Hurlimann et al. | 324/303 |

FOREIGN PATENT DOCUMENTS 0 649 035 B1  4/1995  European Pat. Off. .........  G01V 3/32

OTHER PUBLICATIONS

Morriss et al., "Hydrocarbon Saturation and Viscosity Estimation from NMR Logging in the Belridge Diatomite," 35th SPWLA Annual Logging Symposium (Jun. 19–22, 1994), pp. 1–24.

Carr et al., "Effects of Diffusion on Free Precision in Nuclear Magnetic Resonance Experiments," *Physical Review*, vol. 94, No. 3 (May 1, 1954), pp. 630–638.

(List continued on next page.)

*Primary Examiner*—Louis Arana
*Attorney, Agent, or Firm*—Pennie & Edmonds LLP

[57] ABSTRACT

An NMR pulse sequence and signal processing method is disclosed for measurement of fast decay response signals from materials containing a fluid state. The proposed pulse sequence and processing method are applicable in borehole NMR logging as well as measurements of attributes of man-made or natural materials. The disclosed pulse sequence comprises a series of short NMR pulse trains separated by intervals which are shorter than the time required for polarization of nuclear magnetization in bulk fluids of the fluid state. By stacking response signals to increase the signal to noise ratio, time domain data is obtained that generally corresponds to transverse decay components as short as about 0.5 ms. Various attributes of the materials being investigated can be derived in a single measurement.

46 Claims, 13 Drawing Sheets

OTHER PUBLICATIONS

*Schlumberger Wireline & Testing,* "Combinable Magnetic Resonance tool reliably indicates water–free production and reveals hard–to–find pay zones," (Jun. 1995).

Morriss et al., "Field Test of an Experimental Pulsed Nuclear Magnetism Tool," SPWLA Annual Logging Symposium (Jun. 13–16, 1993), pp. 1–23.

Coates et al., "Core Data and the MRIL Show—A New Approach to 'Formation Factor,'" National SPWLA Convention (Jun. 15, 1992), pp. 1–15.

Kleinberg et al., "Novel NMR Apparatus for Investigating an External Sample," *Journal of Magnetic Resonance,* (1992) pp. 466–485.

Coates et al., "An Investigation of a Magnetic New Resonance Imaging Log," National SPWLA Convention (Jun. 18, 1991), pp. 1–24.

Howard et al., "Proton Magnetic Resonance and Pore–Size Variations in Reservoir Sandstones," *Society of Petroleum Engineers* (1990), pp. 733–741.

Miller et al., "Spin Echo Magnetic Resonance Logging: Porosity and Free Fluid Index Determination," *Society of Petroleum Engineers* (1990), pp. 321–334.

Kenyon et al., "Pore–Size Distribution and NMR in Microporous Cherty Sandstones," SPWLA Thirtieth Annual Logging Symposium (Jun. 11–14, 1989), pp. 1–24.

*Schlumberger Technology News—Oilfield Bulletin,* "Fifth Generation Nuclear Magnetic Resonance Logging Tool: A Major Advance in Producibility Measurement Technology," (Jul. 1995) (2 pp.).

Akkurt et al., "NMR Logging of Natural Gas Reservoirs," SPWLA 35th Annual Logging Symposium (Jun. 26–29, 1995).

Prammer, M.G., "NMR Pore Size Distributions and Permeability at the Well Site,", *Society of Petroleum Engineers* (Sep. 25, 1995) pp. 55–64.

Chandler et al., "Improved Log Quality with a Dual–Frequency Pulsed NMR Tool," *Society of Petroleum Engineers* (1994) pp. 23–35.

Straley et al., "NMR in Partially Saturated Rocks: Laboratory Insights on Free Fluid Index and Comparision with Borehole Logs," SPWLA Annual Logging Symposium (Jun. 27, 1991) pp. 40–56.

Jackson et al., "Western Gas Sands Project Los Alamos NMR Well Logging Tool Development," Los Alamos National Laboratory (Oct. 1981–Sep. 1982) pp. 1–28.

Clavier et al., "The Theoretical and Experimental Bases for the 'Dual Water' Model for the Interpretation of Shaly Sands," *Journal of Petroleum Technology* (Apr. 1984), pp. 3–15.

Waxman et al., "Electrical Conductivities in Oil–Bearing Shaly Sands," *Society of Petroleum Engineers Journal* (1968) pp. 107–122.

PULSE SEQUENCES AND INTERPRETATION TECHNIQUES FOR NMR MEASUREMENTS

CROSS-REFERENCES TO RELATED APPLICATIONS

This application claims the benefit of U.S. Provisional Application No. 60/013,484 filed Mar. 15, 1996.

FIELD OF INVENTION

The present invention concerns nuclear magnetic resonance (NMR) pulse sequences used in evaluating earth formations or various porous materials having a fluid state. More specifically, the invention relates to NMR pulse sequences and methods for interpretation of NMR logging data for estimating earth formation properties, such as the total formation porosity, and/or properties of the porous materials under investigation.

BACKGROUND OF THE INVENTION

No single logging tool or measurement technique is presently available that can correctly identify properties of the rock formation, such as its porosity, in all circumstances. For example, bulk density measurements can only be used if the density of the rock matrix is known; sonic transit time measurements may be used if the transit times both for the rock and the fluids are known. A number of techniques, referred to as "crossplot techniques", exist that compare different measurements to estimate formation porosity in situ. However, none of these techniques is truly independent of the rock's geological make-up.

Another approach frequently used during open-hole logging is to perform bulk conductivity measurements in order to identify and separate oil-bearing zones which have low conductivity, from water-bearing zones which have high conductivity. However, in practice the interpretation of measurement data is typically obscured by the presence of highly-conductive clay attached to or interspersed with sand grains. Due to the fact that no simple measurement exists for generating quantitative in situ estimates of the amount of clay and the water volume bound to the clay, the interpretation of in situ conductivity data is still more of an art than a science.

The amount and type of clay in a formation is interesting to reservoir and to production engineers in its own right. For example, swelling and/or dislodging of certain clay particles may clog an otherwise permeable sand. Conventional logging tools have been often characterized in terms of their response to clay minerals and/or clay-bound water. In fact, most conventional logging measurements (such as neutron-absorption cross section, bulk density, natural gamma-ray radiation, spontaneous electric potential, sonic wave transit time, photoelectric absorption factor, etc.) respond in a qualitative way to the presence of clay in the formation being investigated, mostly because clays tend to accumulate heavy minerals. More information is contained in D. V. Ellis, "Well Logging For Earth Scientists," Elsevier 1987, chapter 19: "Clay Typing and Quantification from Logs," which chapter is incorporated herein by reference. Still, no single reliable method exists currently for estimating the parameters of the clay present in a formation. FIG. 1 shows the standard rock porosity model which provides an illustration of the issues discussed above. In particular, as shown in FIG. 1, the total porosity space is occupied by water and hydrocarbons. The volume excluded from what is designated in the figure as "effective porosity" is the clay-bound water fraction.

It is well known that the signal measured by NMR logging tools is proportional to the mean density of hydrogen nuclei in the fluid that occupies the pore space. Pulsed NMR measurements performed downhole are sensitive to the amount of hydrogen atoms from liquid or gaseous materials, but not from solid-state rock. Therefore, in principle, NMR is a truly lithology-independent porosity measurement. However, with reference to FIG. 1, current logging tools register only part of the total porosity of the formation because hydrogen nuclei in the rock matrix and those associated with clay particles relax too rapidly to be detected and measured under the limited signal-to-noise (SNR) conditions available downhole.

Accordingly, it is clear that the difference between a "total porosity" measurement (derived, for example, from a bulk density measurement, neutron absorption and/or sonic transit time) and the NMR-measured porosity can be interpreted as the amount of clay-bound water. See for example the disclosure in U.S. Pat. No. 5,557,200 assigned to the assignee of the present application, which is hereby incorporated by reference for all purposes. However, prior art methods require the use of separate techniques to measure the total porosity of a formation. In fact, obtaining an accurate estimate of this total porosity is still relatively difficult. Furthermore, an NMR measurement itself can be depressed by fluid effects, such as deficient hydrogen index, long polarization times T1, etc.

It has been recognized in the past that specific applications of NMR logging can be performed with less than full recovery of magnetization. For example, U.S. Pat. No. 5,389,877 to Sezginer et al. describes a method by which a moving NMR logging tool is used to quantify the amount of capillary-bound fluid volume BFV. However, in the patented method the clay-bound volume is not recorded, nor is the log interpretation improved. The patent merely records a sub-set of the data required for interpreting an NMR log. In particular, it requires that other logging tools provide an estimate of total porosity of the formation.

The method of the present invention, described in greater detail below, uses prior art logging tools and measurement apparatuses to obtain previously unavailable data relating to the composition of a geologic structure. In particular, a novel pulse sequence, signal processing technique and a method of interpretation of NMR measurements are proposed and used to obtain in a single experiment characteristics of the formation including its total porosity and clay mineral content which may then be used to determine additional key petrophysical parameters. In addition, the method of the present invention can also be used to measure properties of various porous materials having a fluid state.

Additional references which provide further background information include:

1. Ellis, D. V.: *Well Logging for Earth Scientists*, Elsevier, New York, N.Y. (1987) 305.
2. Miller, M. N. et al.: "Spin Echo Magnetic Resonance Logging: Porosity and Free Fluid Index Determination," paper SPE 20561 presented at the 1990 SPE Annual Technical Conference and Exhibition, Proceedings, 321.
3. Morriss, C. E. et al.: "Field Test of an Experimental Pulsed Nuclear Magnetism Tool," paper GGG presented at the 1993 Annual Logging Symposium of the Society of Professional Well Log Analysts.
4. Chandler, R. N. et al.: "Improved Log Quality With a Dual-Frequency Pulsed NMR Tool," paper SPE 28365 presented at the 1994 SPE Annual Technical Conference and Exhibition, Proceedings, 23.
5. Ellis, D. V.: *Well Logging for Earth Scientists*, Elsevier, New York, N.Y. (1987) 439–469.

6. Korringa, J., Seevers, D. O. and Torrey, H. C.: "Theory of Spin Pumping and Relaxation in Systems With a Low Concentration of Electron Spin Resonance Centers," *Phys. Rev.* 127 (1962) 1143.
7. Fripiat, J et al.: "Thermodynamic and Microdynamic Behavior of Water in Clay Suspensions and Gels," *J. Colloid. Interface Sci.* 89 (1982) 378.
8. Woessner, D. E.: "An NMR Investigation Into The Range of the Surface Effect on the Rotation of Water Molecules," *J. Magn. Reson.* 39 (1980) 297.
9. Prammer, M. G.: "NMR Pore Size Distributions and Permeability at The Well Site," paper SPE 28368 presented at the 1994 SPE Annual Technical Conference and Exhibition, Proceedings, 55.
10. Freedman, R. and Morriss, C. E.: "Processing of Data From an NMR Logging Tool," paper SPE 30560 presented at the 1995 SPE Annual Technical Conference and Exhibition, Proceedings, 301.
11. Prammer, M. G. et al.: "Lithology-Independent Gas Detection by Gradient-NMR Logging," paper SPE 30562 presented at the 1995 SPE Annual Technical Conference and Exhibition, Proceedings, 325.
12. van Olphen, H. and Fripiat, J. J.: *Data Handbook for Clay Minerals and Other Non-Metallic Minerals,* Pergamon Press, New York, N.Y. (1979).
13. Hower, J. and Mowatt, T. C.: "The Mineralogy of Illites and Mixed-Layer Illite Montmorillonites," *The American Mineralogist,* 51, (May–June 1966) 825.

SUMMARY OF THE INVENTION

The present invention defines a novel pulse sequence, logging technique and a signal processing scheme that employ existing NMR instruments or logging tools to directly quantify the amount of bound water in the materials under investigation, or clay-bound water in the formation. The method of the present invention is characterized by the rapid accumulation of only those NMR signal components which are typical for clay-bound water and have very fast T1 and/or T2 relaxation times. The signal-to-noise ratio can typically be enhanced by a factor of seven or more, compared to the standard NMR measurement.

The signal processing scheme extracts very fast decaying components from the high-SNR measurement and combines the measurement of these components with the standard NMR measurement to completely characterize the distribution (or compartmentalization) of the various components of the total porosity in the rock under investigation.

Finally, in accordance with the present invention one can improve the resistivity interpretation model based on the use of parallel conduction paths for clay-bound water and non-clay-bound water. Specifically, having obtained each fluid volume from the NMR measurement separately simplifies the log interpretation and provides more accurate estimates of all parameters of interest. Additional properties of materials under investigation can be obtained by combining the measurements in accordance with the present invention with external measurements, as known in the art.

In a particular embodiment of the present invention, a nuclear magnetic resonance (NMR) method is disclosed for measuring an indication of attributes of materials containing a fluid state, the method comprising the steps of:

(a) applying in a pre-determined sequence at least two short NMR pulse trains, each pulse train comprising at least one pulse and resulting in at least one response signal from said materials, the interval $T_s$ between any two short pulse trains being less than the time required for polarization of substantially all nuclear magnetization in bulk fluids of the fluid state contained in said materials; and (b) stacking NMR response signals from said at least two short NMR pulse trains to obtain time domain data indicative of fast decay components of the fluid state contained in said materials.

In an separate embodiment of the present invention an NMR borehole logging method is disclosed for measuring an indication of petrophysical attributes of an earth formation, the method comprising the steps of:

(a) applying in a pre-determined sequence at least two short NMR pulse trains, each pulse train comprising at least one pulse and resulting in at least one response signal from said earth formation, the interval $T_s$ between any two short pulse trains being less than the time required for polarization of substantially all nuclear magnetization in any bulk fluid contained in said earth formation; and (b) stacking NMR response signals from said at least two short NMR pulse trains to obtain time domain data indicative of fast decay components of a fluid state contained in said earth formation.

DETAILED DESCRIPTION OF THE PREFERRED EMBODIMENT

There are two versions of modern pulse-NMR logging tools in use today: the centralized MRIL® tool made by NUMAR Corporation, and the side-wall CMR tool made by Schlumberger. The MRIL® tool is described, for example, in U.S. Pat. No. 4,710,713 to Taicher et al. and in various other publications including: "Spin Echo Magnetic Resonance Logging: Porosity and Free Fluid Index Determination," by Miller, Paltiel, Millen, Granot and Bouton, SPE 20561, 65th Annual Technical Conference of the SPE, New Orleans, La., Sept. 23–26, 1990; "Improved Log Quality With a Dual-Frequency Pulsed NMR Tool," by Chandler, Drack, Miller and Prammer, SPE 28365, 69th Annual Technical Conference of the SPE, New Orleans, La., Sept. 25–28, 1994). Details of the structure and the use of the MRIL® tool are also discussed in U.S. Pat. Nos. 4,717,876; 4,717,877; 4,717,878; 5,212,447, 5,280,243, 5,309,098, and 5,412,312, all of which are commonly owned by the assignee of the present invention.

The Schlumberger CMR tool is described, for example, in U.S. Pat. Nos. 5,055,787 and 5,055,788 to Kleinberg et al. and further in "Novel NMR Apparatus for Investigating an External Sample," by Kleinberg, Sezginer and Griffin, J. Magn. Reson. 97, 466–485, 1992.

The content of the above patents and publications is hereby expressly incorporated by reference. It should be understood that the present invention is equally applicable to both hardware configurations discussed above, as well as to generic instruments for measuring NMR signals.

Figure 2:
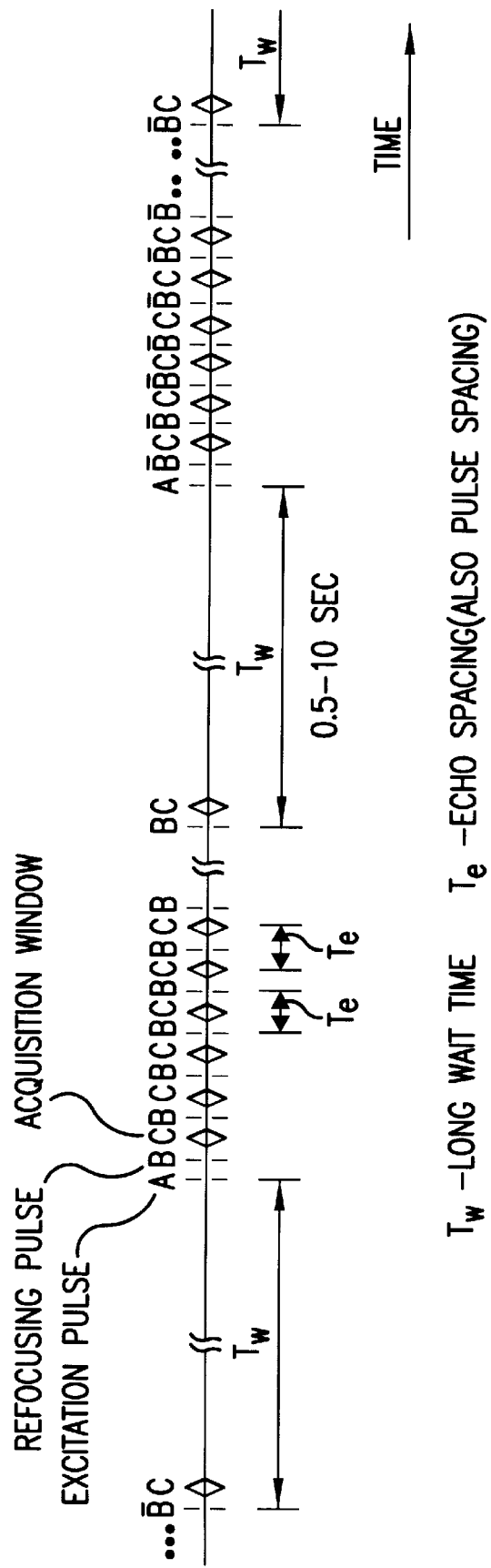
FIG. 2 illustrates a phase-cycled CPMG pulse sequence used with conventional NMR logging tools.

With reference to the attached drawings, FIG. 2 shows a standard pulse sequence typically employed by NMR logging tools, such as the Numar MRIL® and the Schlumberger CMR tools. As shown in FIG. 2, a wait time interval ($T_w$) of approximately 0.5–10 sec is used first to allow for polarization of the formation by the tool's static magnetic field. Then, a Carr-Purcell-Meiboom-Gill (CPMG) pulse-echo train is executed, consisting of an excitation pulse (A) and an alternating sequence of refocusing pulses (B). Following each pair of excitation pulse and a refocusing pulse, acquisition window (C) is applied next. Complex data from such a pair of echo trains are co-added on an echo-by-echo basis to remove certain artifacts and to enhance the NMR signal, as known in the art. More pairs may be added to enhance the signal-to-noise ratio. The echo train, consisting of a superposition of exponentially decaying signals is then submitted to a processing scheme which calculates the underlying decay modes of the received NMR echo signal.

Specifically, a processing method (Prammer's method) for calculating the underlying decay modes of the NMR signal is described in U.S. Pat. No. 5,517,115 to the present inventor. The content of this patent is hereby expressly incorporated by reference for all purposes. As discussed in the patent, if such a measurement is repeated many times while the tool is held stationary, it is possible to identify the portion of the clay-bound water in the signal.

NMR RESPONSE OF CLAY-BOUND WATER

Figure 1:
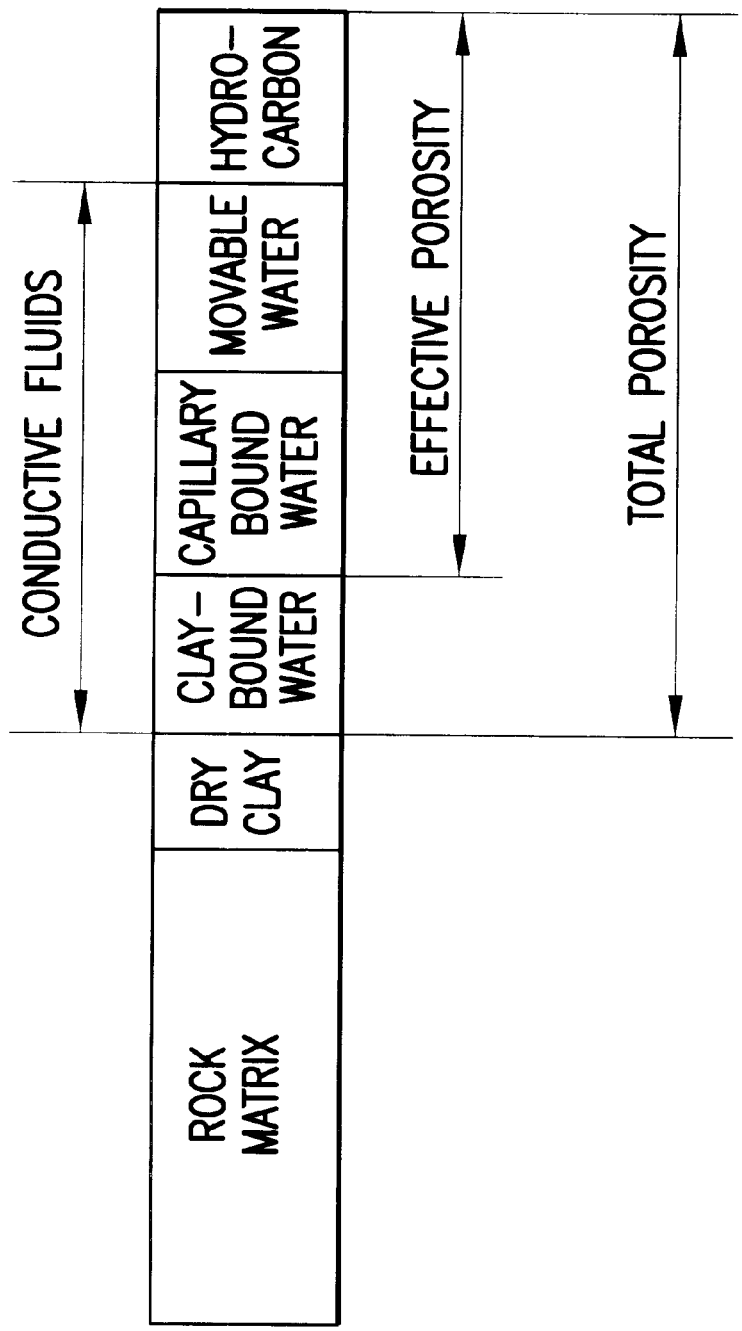
FIG. 1 shows the standard rock porosity model which illustrates the principles behind the present invention.

As discussed above with reference to the rock porosity model in FIG. 1, conventional hydrogen-NMR responds well to hydrogen in fluids and very poorly or not at all to hydrogen in solids. Thus, downhole NMR logging is only concerned with the fluid-filled porosity of the rock space. The rate of signal decay is a strong function of the local surface-to-volume ratio in the pore space. Both $T_1$ (longitudinal) and $T_2$ (transversal) relaxation times, which are on the order of a few seconds in fresh water, can be reduced by several orders of magnitude once the liquid is introduced into the pore space and is in contact with the grain surfaces. The effect has been explained in physical terms by the theory of surface relaxation. The first generation of NMR logging tools was limited to an intrinsic "dead time" of 20 ms, corresponding to a $T_2$ cutoff time of about 30 ms, which in many shaly sand formations separates irreducible from movable fluids. Today's commercial pulsed-NMR tools also quantify the capillary-bound ("irreducible") regime in the $T_2$ range of 4–30 ms.

Clay-bound water, however, has much faster $T_2$ times due to the enormous specific surface area of clays (up to 800 $m^2/g$). Details on specific surface areas and NMR measurements on smectites and kaolinites can be found in Fripiat et al. D. E. Woessner has studied longitudinal relaxation times ($T_1$) at 8 and 25 MHz in aqueous solutions of hectorite. He found a perfectly linear relationship between the relaxation rate ($1/T_1$) and the amount of dry clay per water volume. The plausible explanation for these data is the combination of two factors: (1) a short-range dipole-dipole surface relaxation effect that does not extend more than 1–2 layers of water molecules from the solid surface, and (2) fast exchange between this mono-molecular surface water layer and the clay-associated water volume due to thermal diffusion.

In order to more closely resemble the downhole measurement, laboratory NMR experiments were performed at 1 MHz to determine transverse relaxation times $T_2$. Representative samples of montmorillonite (a smectite), illite, kaolinite and chlorite were obtained from the Source Clay Minerals Repository of the Clay Mineral Society, located at the University of Missouri. Table 3 summarizes the sample clay types and their properties. The samples were prepared by adding 0%, 12.5%, 25% and 50% by weight of synthetic sea-water brine, mixing the paste and pressing the mixture at 2500 psi. NMR amplitudes and $T_2$ distributions of the sealed samples were measured in a commercially available core analyzer, operating at 1 MHz, a temperature of 25° C., and at echo spacings ($T_e$) of 0.3 ms and 0.5 ms. The water content was determined by weighing each sample before and after overnight vacuum-drying at 103° C. The results are listed in Table 4.

Except for the montmorillonite sample SWy-2, no clay sample had an NMR signal without having water added to it. SWy-2 absorbs 7% water by weight under normal indoor humidity conditions. At this concentration, the bound water relaxes extremely fast with poor visibility at the 0.5 ms echo spacing. As more brine is added, $T_2$ increases up to 1 ms, while all absorbed water becomes NMR-visible. The latter fact is consistent with the "fast exchange" hypothesis borne out of Woessner's data. The clay-bound water in the other clay samples is always fully visible at $T_e$=0.5 ms. As expected, $T_2$ increases linearly with the amount of water absorbed. The illite sample could not absorb more than 15.8% brine, the kaolinite was limited to 20.0% and the chlorite to 7.5%. Selected $T_1$ measurements were performed, yielding ratios of $T_1/T_2$ between 1.5 and 2 as indicated in Table 4.

The "fast exchange" hypothesis predicts a linear relationship between relaxation rate and the surface-to-volume ratio:

$$\frac{1}{T_2} = \rho_2 \frac{A}{V} \quad (1)$$

The laboratory measurements allow one to estimate values for the surface relaxivity $\rho_2$ from specific surface areas (Table 3) and from the water-to-dry ratios (Table 4). As shown in Table 4, the computed values are almost constant (0.8–1 $\mu$m/s), except for the chlorite sample, which is probably compromised by an overestimated specific surface area. Apparently, clay mineralogy has little influence on the $T_2$ values, but rather the surface-to-volume ratio is the dominant factor. Furthermore, these values for surface relaxivity are substantially smaller than those reported in the literature for sandstones (of the order of 5–20 μm/s). Fortunately for a downhole measurement, the low surface relaxivities of clays imply a range of $T_2$ values that can be measured with the current MRIL logging tool technology.

The cation exchange capacity (CEC, Table 3) of clays is fundamental to the conversion of bulk resistivity measurements into water saturation and hence hydrocarbon saturation estimates. The number of available exchange sites is proportional to a clay's specific surface ratio, and therefore the observed $T_2$ can be turned into an indicator of CEC: $T_2$ components greater than 3 ms indicate little or no CEC; the range 1–2 ms is associated with illite-type CEC's, and $T_2$'s less than 1 ms indicate smectites with high CEC values.

A field study was conducted at Shell's Stribling #1 test well near Johnson City, Tex., to confirm the laboratory $T_2$ data and to prove the concept of a downhole clay-bound water measurement. The well was drilled and cored in 1964 and is open-hole from casting at 305 ft to total depth at 1268 ft. Its geological composition is well characterized, consisting of shaly sands and shales below 1100 ft. The heavy and variable clay contents made this well very suitable for the present study. Illite as the dominant clay mineral in these formations.

Figure 3:
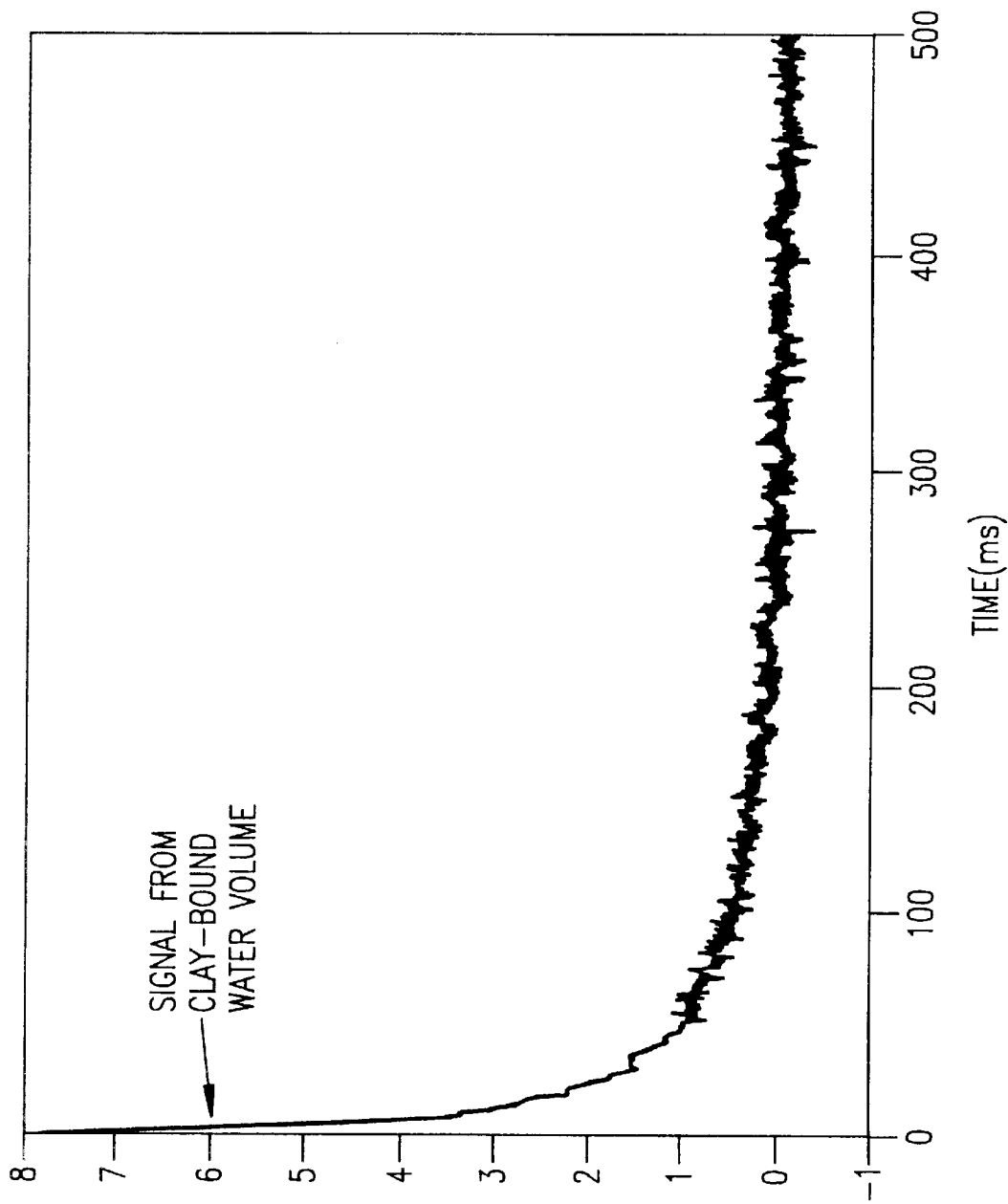
FIG. 3 illustrates the accumulated result of 300 NMR measurements using Numar's MRIL® tool.

An MRIL engineering test tool was used to acquire station logs in the various shaly sandstone sections. FIGS. 2 and 3 show representative data collected at a station opposite a formation with about 50% bioturbated shale. Carr-Purcell-Meiboom-Gill echo trains with 1000 data points and an echo-to-echo spacing of 0.51 ms were acquired and averaged for 15 minutes in order to increase the signal-to-noise ratio, i.e. the precision of the measurement. The very fast initial decay visible in FIG. 2 has a time constant of 1 ms and is due to clay-bound water.

FIG. 3 illustrates the accumulated result of 300 actual measurements from NUMAR's MRIL® tool, each measurement consisting of about 1000 echoes with an echo-to-echo spacing of 510 microseconds.

Figure 4:
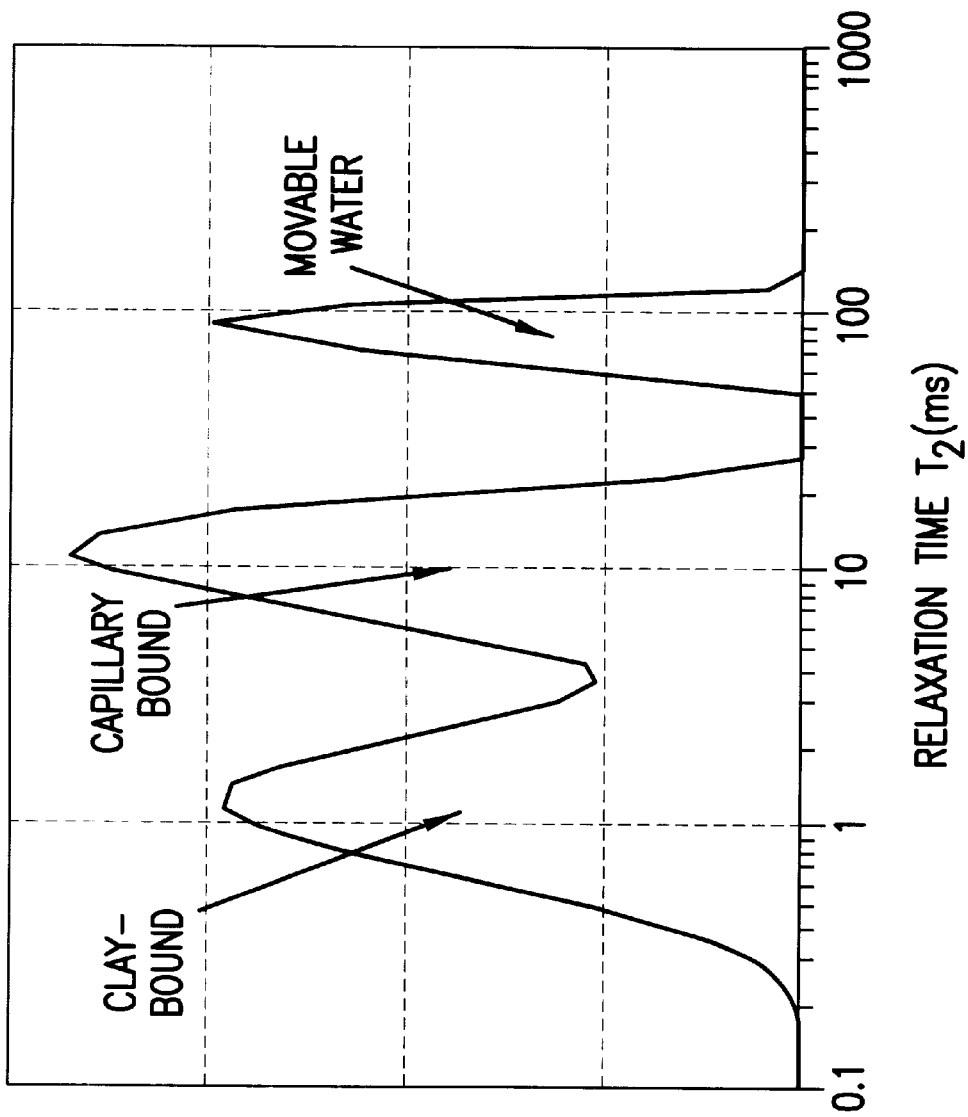
FIG. 4 illustrates the result of applying Prammer's processing method to the data shown in FIG. 3.

FIG. 4 illustrates the result of applying Prammer's processing method to the data shown in FIG. 3. Each peak in this "relaxation spectrum" shown in FIG. 4 corresponds to a major relaxation mode of the underlying signal. In particular, from left to right one can identify three peaks: (a) clay-bound water, (b) capillary bound water and (c) movable water. In accordance with the Prammer's processing method the integrated areas under the peaks are proportional to the individual water volumes. In the example illustrated in FIG. 4, the amount of clay-bound water volume is 4.8%; capillary-bound water volume is 4.9%; and movable water volume is 1.8% of the total volume.

FIG. 4 also illustrates the customary T2 "cutoff" values which, in this example are 3 ms for the clay vs. non-clay boundary and 30 ms for non-movable vs. movable water. While these cutoff values are not universally applicable, they are fairly standard in the logging industry for use in oil reservoirs in shaly sandstone foundations.

In the stationary example illustrated in FIG. 4 it took about 15 minutes to accumulate the stationary data. In a moving tool, of course, much less time is available for accumulation. Therefore, given that the achievable signal-to-noise ratio is limited by basic physical parameters and the tool construction, less information can be extracted from the log data. In particular, $T_2$ information below 3 ms becomes very unreliable and "regularization" schemes must be applied to suppress very fast relaxation modes in the data.

The present invention consists of three parts: development of a novel pulse sequence, data processing and measurement interpretation.

Figure 5:
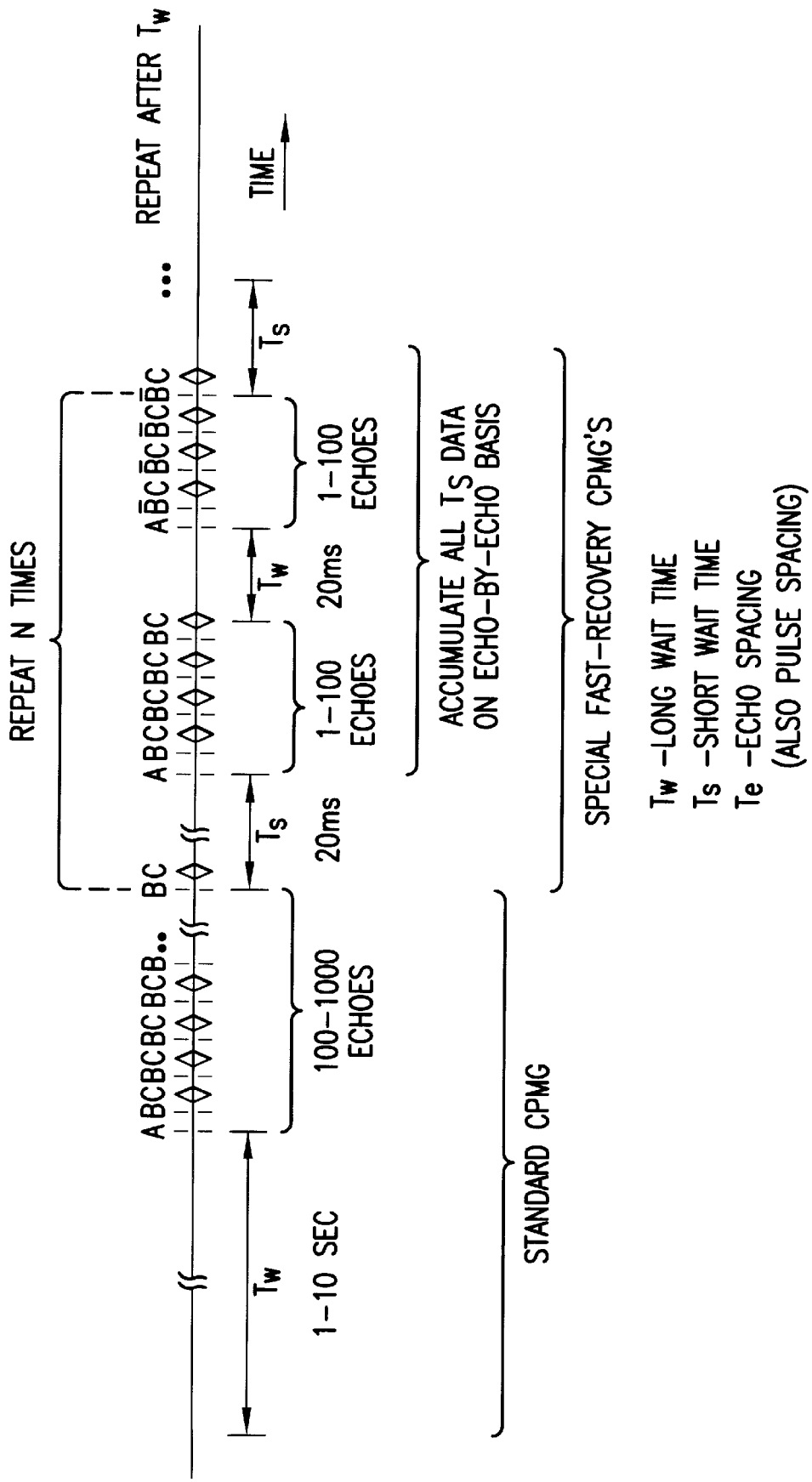
FIG. 5 illustrates the novel NMR pulse sequence in accordance with a preferred embodiment of the present invention.

The novel pulse sequence in accordance with a preferred embodiment of the present invention is shown in FIG. 5. The first part of the sequence is identical to the one shown in FIG. 2. As shown in FIG. 5, immediately following the regular CPMG train is issued a series of short echo trains characterized by short wait intervals ($T_s$). Preferably, about 0.5–10 seconds are required for the long wait period $T_w$, followed by a standard CPMG pulse-echo train of several 100 ms duration, followed by a short wait time $T_s$ having about 10–100 ms duration. The short wait time $T_s$ is followed next by a CPMG train having about 1–100 echoes, which is followed by another short wait time, and so forth. In a specific example, 16 echoes can be used. Typically, for every long pulse train, between about 10 to 100 short echo trains are used. The sequence of short pulse trains is phase-cycled, i.e., alternate trains use phase-reversed refocusing pulses. All echoes from the short trains are co-added to yield several final short recovery data points. In a specific example using 16 echoes, corresponding number of short recovery data points are generated.

Figure 6:
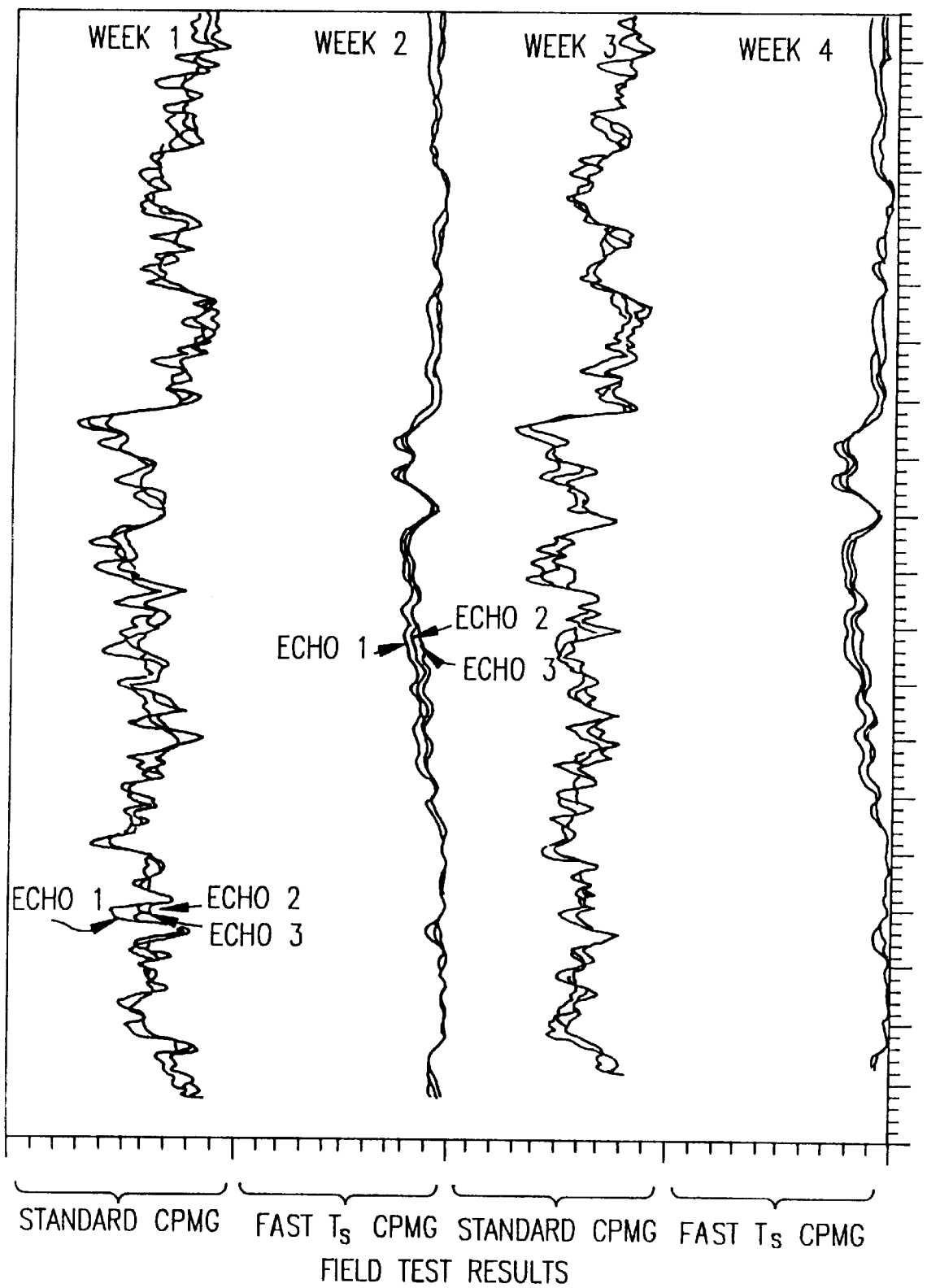
FIG. 6 illustrates results from a field test using the novel NMR pulse sequence shown in FIG. 5.

Results from a field test of the novel pulse sequence shown in FIG. 5 are illustrated in a specific example in FIG. 6. In this example, standard echo data and short-recovery data were acquired on separate passes, but at the same logging speed (5 ft/min) and over the same depth interval. In an alternative embodiment of the present invention both measurements can be performed simultaneously resulting in obvious advantages in terms of speeding up the measurement process. Track 1 in FIG. 6 presents the first three echoes from the standard echo train. The echo-to-echo spacing used in this example was 1.2 ms. The effect of thermal noise in this experiment is clearly seen from fact that later echoes are sometimes higher than earlier ones which would not be the case with noiseless data.

Track 2 in FIG. 6 illustrates the first three echoes resulting from co-adding 50 short-recovery measurements in place of a single standard measurement. The echo-to-echo spacing in this experiment was 0.51 ms. The signal-to-noise ratio for the short-recovery measurements was improved by a factor of $\sqrt{(50)} \approx 7$ over the standard log. Notably, the echo amplitudes in track 2 are depressed compared with those in track 1, because they are associated with fast $T_1$ recovery. Tracks 3 and 4 present two more logging passes over the same depth interval, and are equivalent to tracks 1 and 2, respectively.

In accordance with a preferred embodiment of the present invention the signals obtained above are processed using a method illustrated in FIG. 7 and summarized as follows:

(A) The standard CPMG data obtained in block 10 is subjected in block 20 to the $T_2$ inversion procedure outlined in U.S. Pat. No. 5,517,115, using a pre-specified model of principal $T_2$ relaxation components. For example, the numerical sequence: 4, 8, 16, 32, 64, 128, 256, 512, 1024, 2048 ms can be used in a specific embodiment. Block 50 in FIG. 7 indicates the $T_2$ relaxation spectrum obtained on output of block 20. The sum of all detected modes obtained in block 60 is designated as the effective, or standard NMR porosity. The $T_2$ relaxation spectrum in block 50 is used to differentiate capillary-bound water from movable fluids (water or hydrocarbons).

(B) The accumulated fast-$T_s$ short echo trains in block 30 are subjected in block 40 to $T_2$ inversion using another pre-specified set of relaxation components. In the specific embodiment illustrated in FIG. 7, the sequence: 0.5, 1, 2, 4, 8, 2048 ms, of relaxation components was used. In this example, amplitudes found to relax with 4, 8 or 2048 ms are discarded as being incompletely polarized. On the other hand, the amplitudes associated with 0.5, 1 and 2 ms relaxation times represent the fast relaxation spectrum (block 50) and are next summed in block 70 to yield what is (tentatively) equated to "clay-bound porosity."

Figure 7:
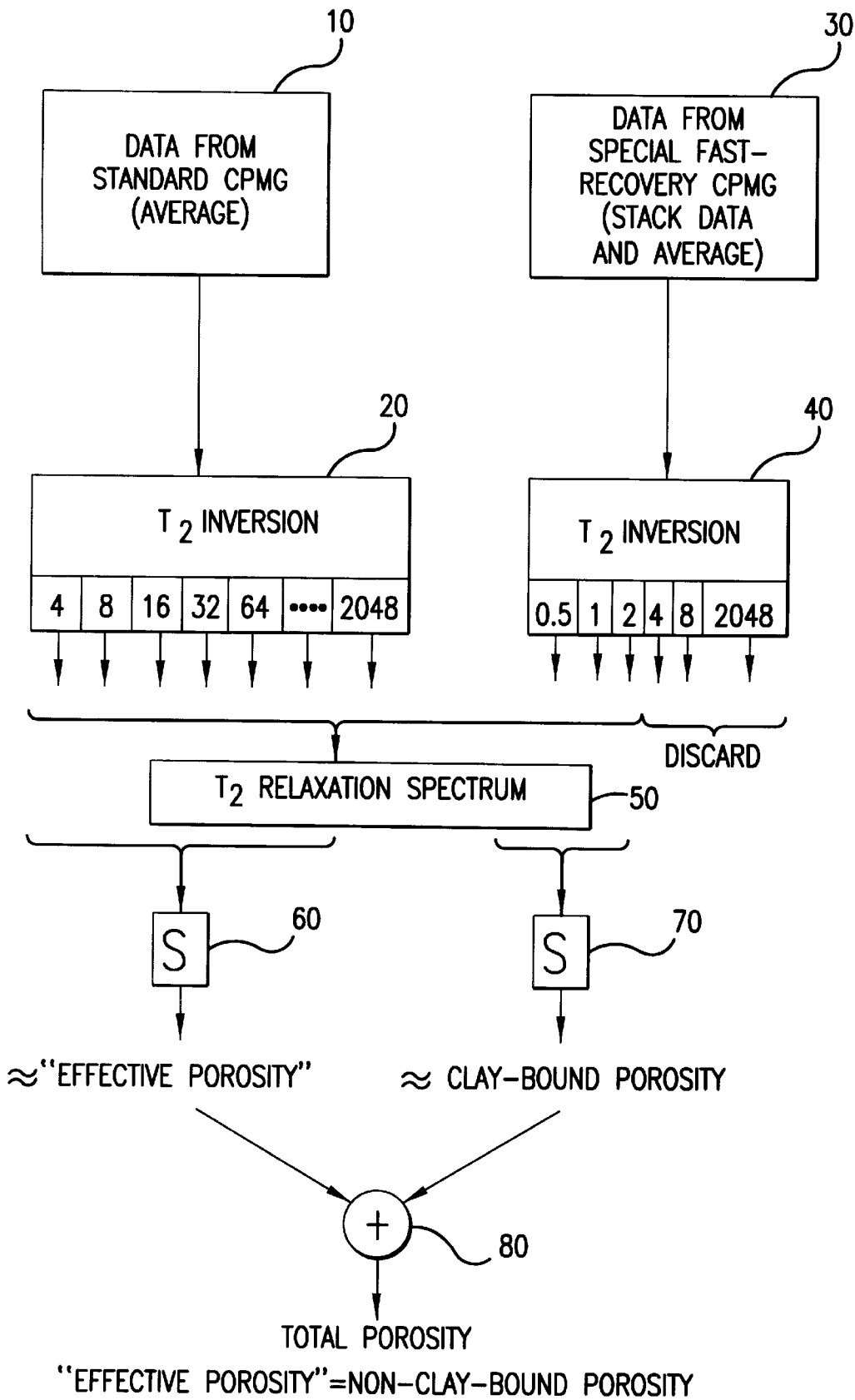
FIG. 7 illustrates in a block-diagram form the method of processing NMR signals in accordance with a preferred embodiment of the present invention.

As shown in FIG. 7, a complete T2 distribution can be assembled in block 50 from concatenated responses in blocks 20 and 40. In the specific example shown, the $T_2$ comprises the 0.5, 1, 2, 4, 8, 16, 32, 64, 128, 256, 512, 1024 and 2048 ms relaxation modes. The sum of all these responses is taken in block 80 as a measure of the total formation porosity. In accepting this measure it is assumed that the rock is completely filled with liquids of hydrogen indices equal to the one of water. Tables 1 and 2 provide a complete listing of the stationary and logging measurement parameters, respectively.

The processing scheme described above with reference to FIG. 7 is an illustration of a preferred embodiment of the present invention, in which the porosity measurements are obtained on the basis of the $T_2$ relaxation spectrum approach. In an alternative embodiment of the present invention, equivalent processing can be done in the time domain. Briefly stated, in this alternative embodiment the "standard" NMR echo data is used to obtain a rough estimate of the time dependency of the early data points. Next, the high-signal-to-noise, high-quality data points from short echo trains are used to refine this estimate and to draw an accurate relaxation curve, interpolated back to time zero. The resulting composite relaxation curve can then be submitted to $T_2$ inversion to produce a unified $T_2$ distribution.

The signal processing method of the present invention allows to determine, in a single measurement experiment, both the total porosity of the formation, and the clay bound porosity which parameters can next be used to obtain additional petrophysical parameters of interest.

MODEL INTERPRETATION

There exist many models for interpreting resistivity measurements in shaly sand formations. Most of these methods incorporate a model of parallel conduction paths for electrical current flowing through water with conductivity $C_w$ and through clay-bound water with conductivity Ccw. The $C_w$ parameter can be deduced from log responses in 100%-water-filled formations or can be measured on produced water samples. Parameter Ccw is frequently modeled is a simple function of temperature using, for example, the formula $$C_{cw}=0.000216*(T_f+504.4)*(T_f-16.7)$$

where Tf is the formation temperature.

Further inputs required in the measurement interpretations are the water saturation associated with $C_w$ ($S_w$) and the water saturation associated with $C_{cw}$ ($S_{wb}$). See, for example the discussion in U.S. Pat. No. 5,557,200 assigned to the assignee of the present application, the content of which is expressly incorporated by reference for all purposes. Both parameters $S_w$ and $S_{wb}$ can be obtained from NMR measurements using the novel pulse sequence and the signal processing method of the present invention.

In particular, as indicated above, the area under the $T_2$ distribution gives the total volume available for fluid accumulation. The "fast" end of the $T_2$ distribution is mostly associated with clay-bound water; the partial "fast $T_2$" area divided by the total area yields the parameter Swb. Similarly, the water saturation $S_w$ can be extracted from the "slow $T_2$" area of a $T_2$ distribution. The proposed method of interpretation represents a significant improvement over the published prior art, in which saturation parameters had to be estimated from separate and often inaccurate measurements.

TIME-DOMAIN ANALYSIS OF COMPOSITE ECHO TRAINS

Figure 8A:
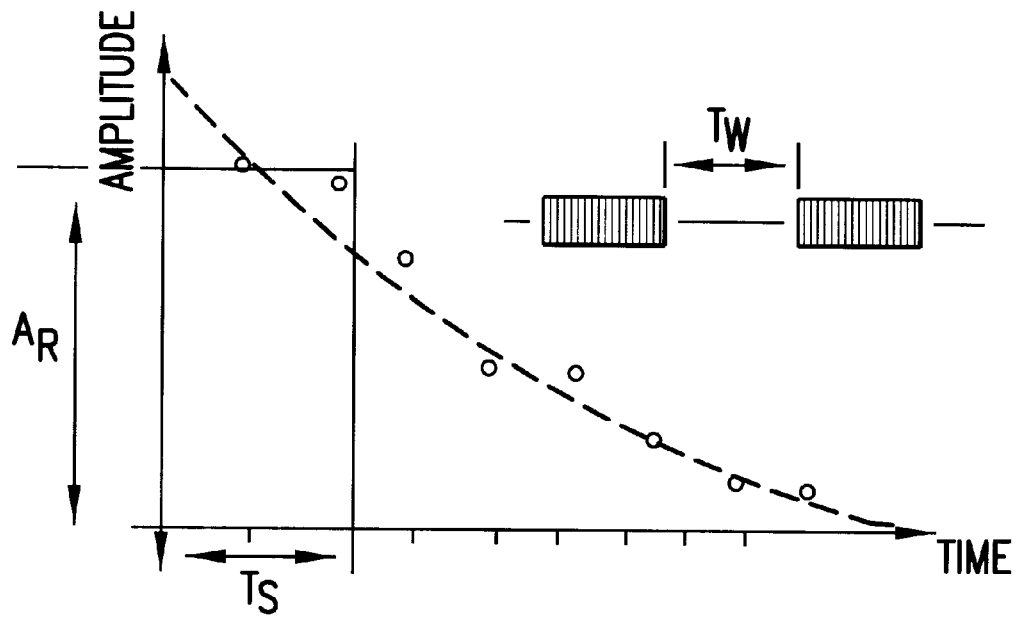
FIG. 8A is a regular pulse/echo train with relatively poor signal-to-noise ratio.

Another preferred embodiment of the present invention involves the use of composite echo trains in which the two separate processing branches of the algorithm illustrated in FIG. 7 are optimized individually. More specifically, consider pairs of echo trains as shown in FIGS. 8A and 8B:

(1) FIG. 8A illustrates a regular set of echoes from a CPMG sequence with a wait time $T_w$ such that $$T_w \geq 3 \times \max(T_1),$$

where max ($T_1$) denotes the highest expected $T_1$ time of the fluid(s).

Figure 8B:
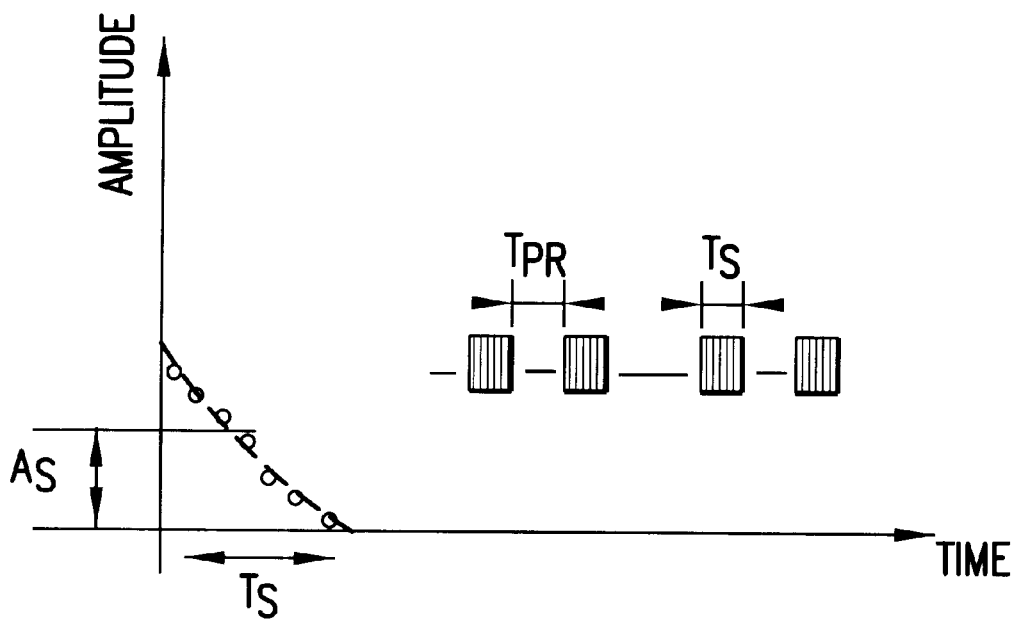
FIG. 8B shows heavily stacked (averaged), short pulse/echo train with high signal-to-noise ratio, in accordance with the method of the present invention.

(2) FIG. 8B illustrates a set of echoes, which is heavily overlapped to give a very high signal-to-noise ratio, obtained by stacking short echo trains with a wait time $T_{PR}$ such that $$T_{PR} << 3 \times \max(T_1).$$

In accordance with a preferred embodiment of the method of the present invention, data obtained as shown in FIGS. 8A and 8B is combined such that:

(1) the information about the long signal decays is retained; and (2) the SNR improvement from the stacked echo train is optimally utilized.

In particular, the regular echo set can be expressed mathematically as $$S_R(t)=\int A(T_2)e^{-t/T_2}d(T_2)+N(0,\sigma_R) \qquad (2)$$

where $A(T_2)$ is a $T_2$ distribution, and N is a normal noise distribution with zero mean and a standard deviation $\sigma_R$. The initial amplitude (time=0) corresponds to full polarization.

The stacked echo set illustrated in FIG. 8B can be expressed mathematically as $$S_S(t) = \int A(T_2)\left(1 - e^{-\frac{T_{PR}}{T_1(T_2)}}\right)e^{-t/T_2}d(T_2) + N\left(0, \frac{\sigma_R}{\sqrt{NA}}\right) \qquad (3)$$

where $A(T_2)$ is the same $T_2$ distribution, $T_{PR}$ is the partial recovery time, $T_1(T_2)$ is the $T_1$ distribution associated with the $T_2$ distribution, and NA is the number of averages used to obtain the data stack. Due to the short repeat time, the initial amplitude does not correspond to full magnetization.

The stacked echo trains span an experiment time $T_s$. Next, in accordance with the method of the present invention, the time-average over the data is formed as follows:

$$A_S = \frac{1}{T_S} \int_0^{T_S} S_S(t) dt \qquad (4)$$

Similarly, the time average $A_R$ for the regular data set is calculated over the same time interval $T_s$ using the expression:

$$A_R = \frac{1}{T_S} \int_0^{T_S} S_R(t) dt \qquad (5)$$

Figure 9A:
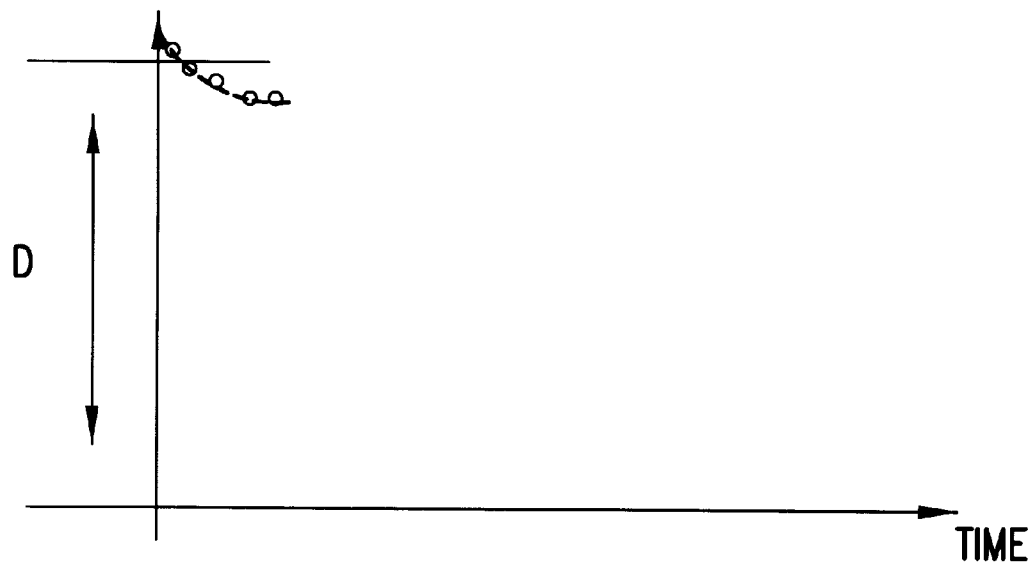
FIG. 9A shows offset stacked train $S_s^*$, used in accordance with the present invention.

The difference D between amplitudes is expressed as $$D = A_R - A_S, \qquad (6)$$

and added to $S_S$ (t) to obtain:

$$S_S^*(t) = S_S(t) + D, \qquad (7)$$

as shown in FIG. 9.

Figure 9B:
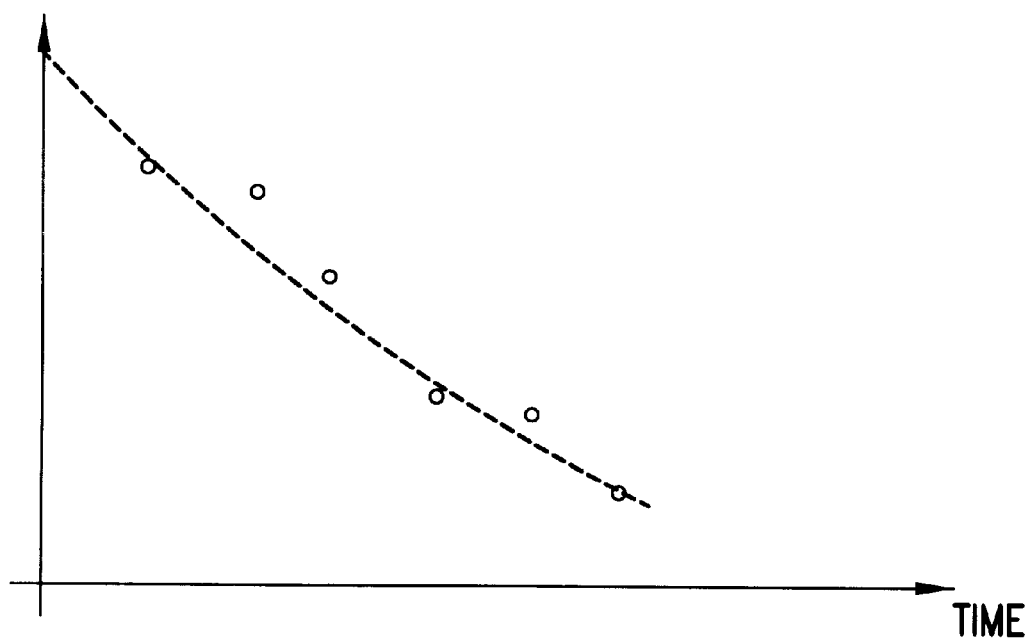
FIG. 9B shows a composite echo train $S_C$.

Finally, echo trains $S_R$ and $S_S^*$ are combined in a composite train $S_C$ illustrated in FIG. 9B, according to the definition:

$$S_C = \begin{cases} S_C^* \text{ for } t < T_S \\ S_R \text{ for } t > T_S \end{cases} \qquad (8)$$

The composite echo train $S_C$ has the high signal-to-noise ratio necessary to extract fast decaying components, and also retains information about the slowly decaying and slowly polarizing components.

A composite $T_2$ distribution can be calculated from the composite train $S_C$ by means of the inversion method disclosed in U.S. Pat. No. 5,517,115 to Prammer.

SHALE VOLUME AND NET-TO-GROSS CALCULATION

Figure 10:
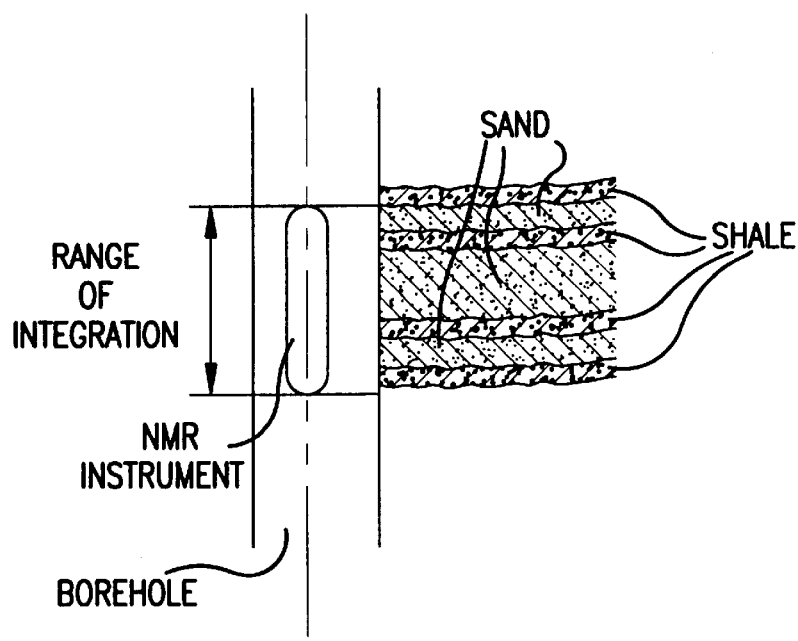
FIG. 10 shows in a diagram form an NMR tool in a borehole which traverses a highly laminated earth formation having layers of sandstone and shale.

Consider an earth formation consisting of laminations of shale and sand, as shown in FIG. 10. Note that the thickness of an individual sand or shale layer may range from approximately 1 mm to many meters and may not always be resolved by the aperture (range of integration) of the NMR instrument. As shown in the art, hydrocarbon fluids can only migrate to and accumulate in the sand layers. In the following description, the following definitions are used:

$\phi_T$—total porosity; integrated over the measuring device's vertical aperture $\phi_{shale}$—shale porosity; integrated $\phi_{sand}$—sand porosity.

The net-to-gross N/G ratio is given by $$N/G = \phi_{sand}/\phi_T. \qquad (9A)$$

The ratio N/G is currently estimated by visual inspection of core samples or by logging with electrical "microimaging" devices that send electrical current through multiple electrodes into the formation. Another way to estimate N/G is from natural radioactivity, because shales tend to be more radioactive than sands.

Figure 11:
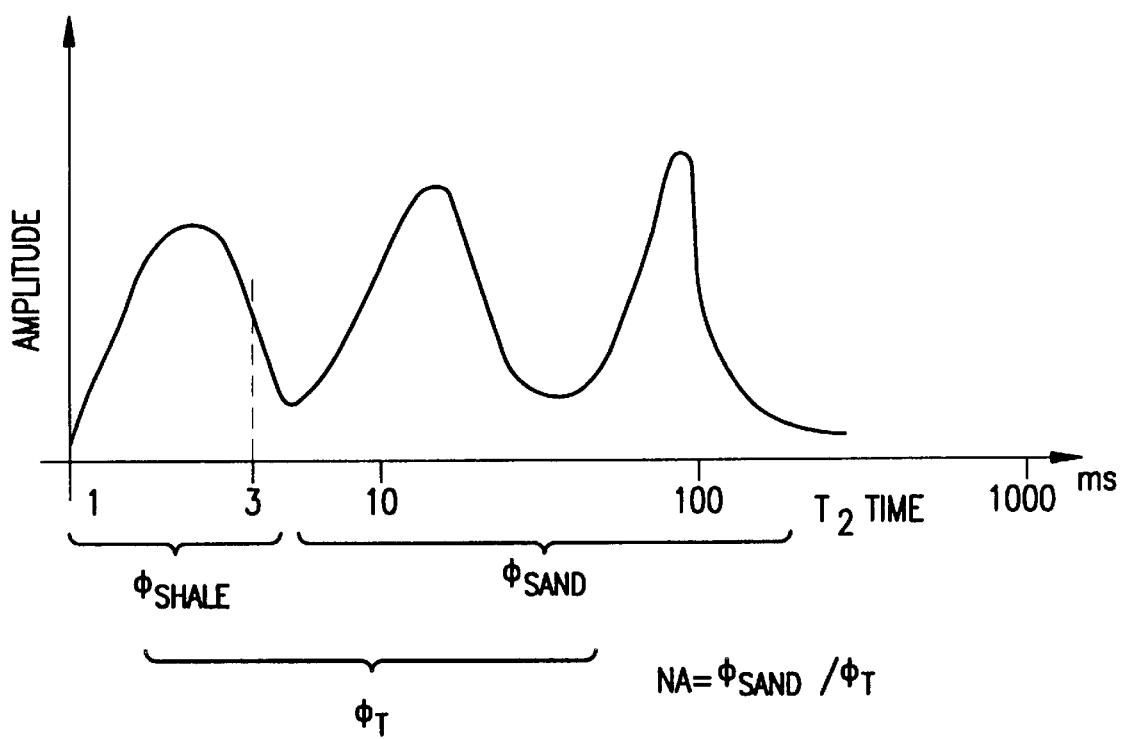
FIG. 11 illustrates an example of $T_2$ spectrum obtained from signals in a laminated sand/shale earth formation.

However, using the method of the present invention, the N/G ratio can be estimated directly as follows. A typical $T_2$ spectrum is shown in FIG. 11. For many clay minerals (illites, smectites), water occupying the shale porosity relaxes with NMR relaxation times less than about 3 ms. Therefore, the part of the $T_2$ spectrum below approximately 3 ms can be identified as shale porosity $\phi_{shale}$; the rest is identified as sand porosity $\phi_{sand}$. The capacity of a reservoir to hold hydrocarbons is proportional to the sand portion of the total porosity. Equation 9A above can be rewritten as:

$$N/G = \frac{\phi_{sand}}{\phi_{shale} + \phi_{sand}} \qquad (9B)$$

ESTIMATION OF CLAY AND SHALE VOLUME

Reference is made to "Measurements of Clay-Bound Water and Total Porosity by Magnetic Resonance Logging" by Prammer et al., The Log Analyst, November/December 1996 pp. 61–69. As shown in this paper, an earth formation can consist of the following components:

1) rock matrix (e.g. Quartz)
2) clay minerals,
3) water bound to clay minerals,
4) capillary-bound fluid,
5) unbound fluids.

The component (3) corresponds to shale porosity $\phi_{shale}$, whereas component (4) is the sand porosity $\phi_{sand}$.

By estimating $\phi_{shale}$ from the $T_2$ spectrum, as discussed above, and by noting the dominant $T_2$ relaxation time of the clay-bound water, an estimate of the clay mineral component type can be obtained from Table 4.

Furthermore, having identified the clay type, by assuring an average water weight-to-dry clay weight ratio, an estimate of the dry clay weight can be obtained. Again, refer to Table 4, columns 2 and 5.

ESTIMATION OF RESERVOIR PRESSURE

In highly laminated reservoirs, as illustrated in a diagram form in FIG. 10, the clay mineral type is fairly uniform. In this case, the relative water content and the average pore size in the shale is dominated by the pressure compacting a shale lamination. The more pressure, the smaller the pore sizes become, resulting in a decrease in $T_2$. By following the trend in shale $T_2$'s vertically, a pressure profile can be obtained, indicative of high or low pressure differentials.

FIELD TEST RESULTS

Field testing to verify the use of the method of the present invention was performed at Amoco's test site CTF-DM #21A in the Catoosa field in Rogers County, Oklahoma. The well was drilled in 1993 to a total depth of 1774 ft. It is open-hole from casing at 162 ft to TD and contains fresh gel mud. Geologically, the well shows sequences of shales, shaly sandstones, limestones and dolomites.

Figure 12:
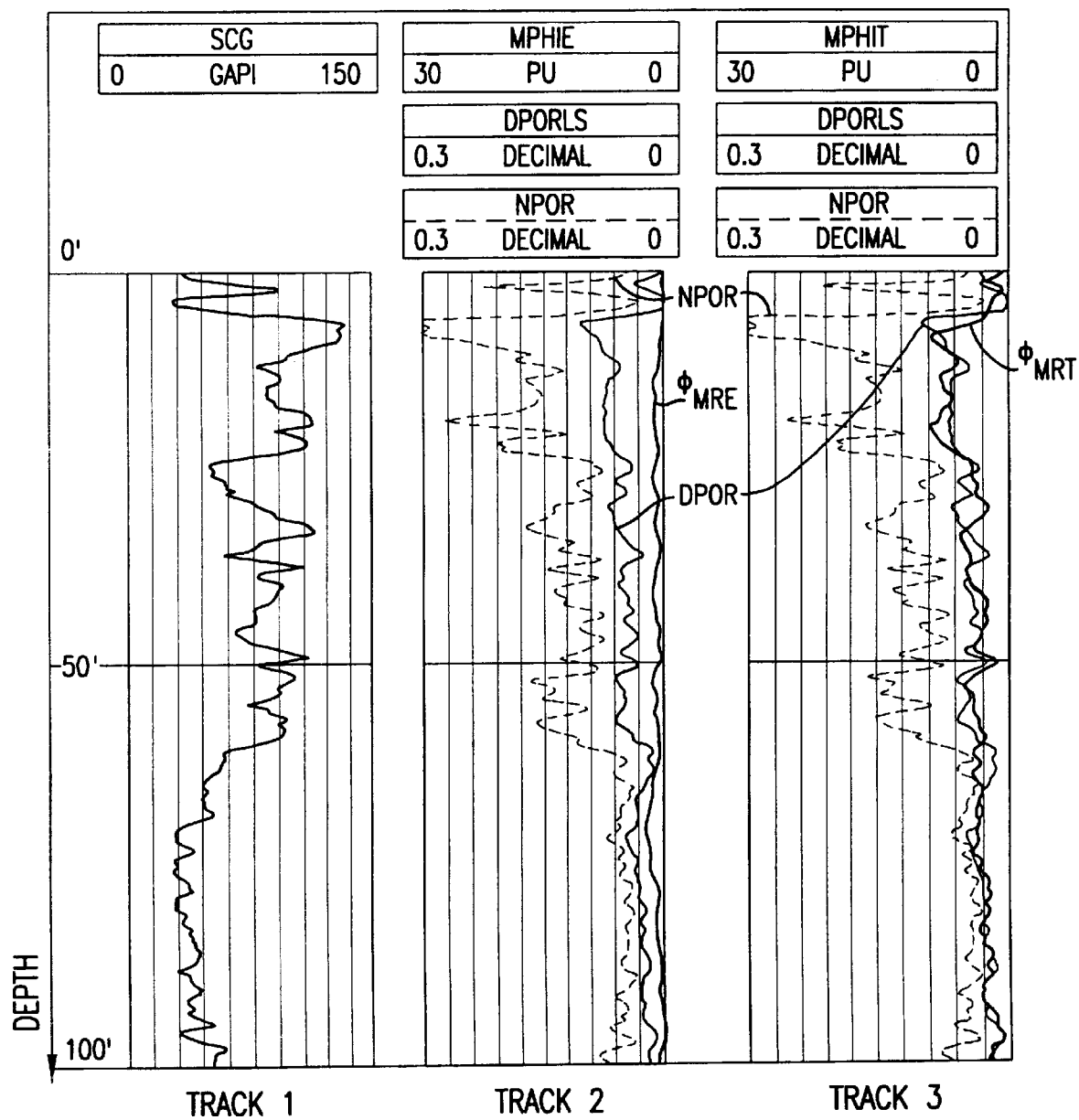
FIG. 12 illustrates the difference between the MRIL effective porosity $\Phi_{MRE}$ and the MRIL total porosity $\Phi_{MRT}$.

The difference between the MRIL effective porosity $\Phi_{MRE}$ and MRIL total porosity $\Phi_{MRT}$ is illustrated in FIG. 12. Shown is the log over a 100 ft shaly section as follows: Track 1: gamma ray in API units (0–150); tracks 2 and 3: porosities on a scale of 0 to 0.3. Density porosity is shown light solid, neutron porosity is dashed. There is almost no effective porosity and $\Phi_{MRE}$ (center track, bold solid) shows little development. On the other hand, $\Phi_{MRT}$ (right track, solid) agrees well with density porosity. All MRIL data was acquired in a single pass using the acquisition sequence shown in FIG. 5.

The second log example (FIG. 13) illustrates the advantages of the lithology-independence of $\Phi_{MRT}$, obtained in accordance with the present invention. In a water-filled or oil-filled formation of unknown lithology, the matrix density can be estimated as follows: Using the total MRIL porosity (in decimal units; $\Phi_{MRT}$ is shown in track 3 as bold line) as the porosity term in the bulk density response, $$\rho_b = \Phi_{MRT}\rho_{fl} + (1-\Phi_{MRT})\rho_{ma}, \quad (10)$$

and setting $\rho_{fl}=1.0$ g/cm$^3$ for water, an apparent matrix density $\rho_{app}$ can be computed:

$$\rho_{app} = \frac{\rho_b - \phi_{MRT}}{1 - \phi_{MRT}}. \quad (11)$$

Figure 13:
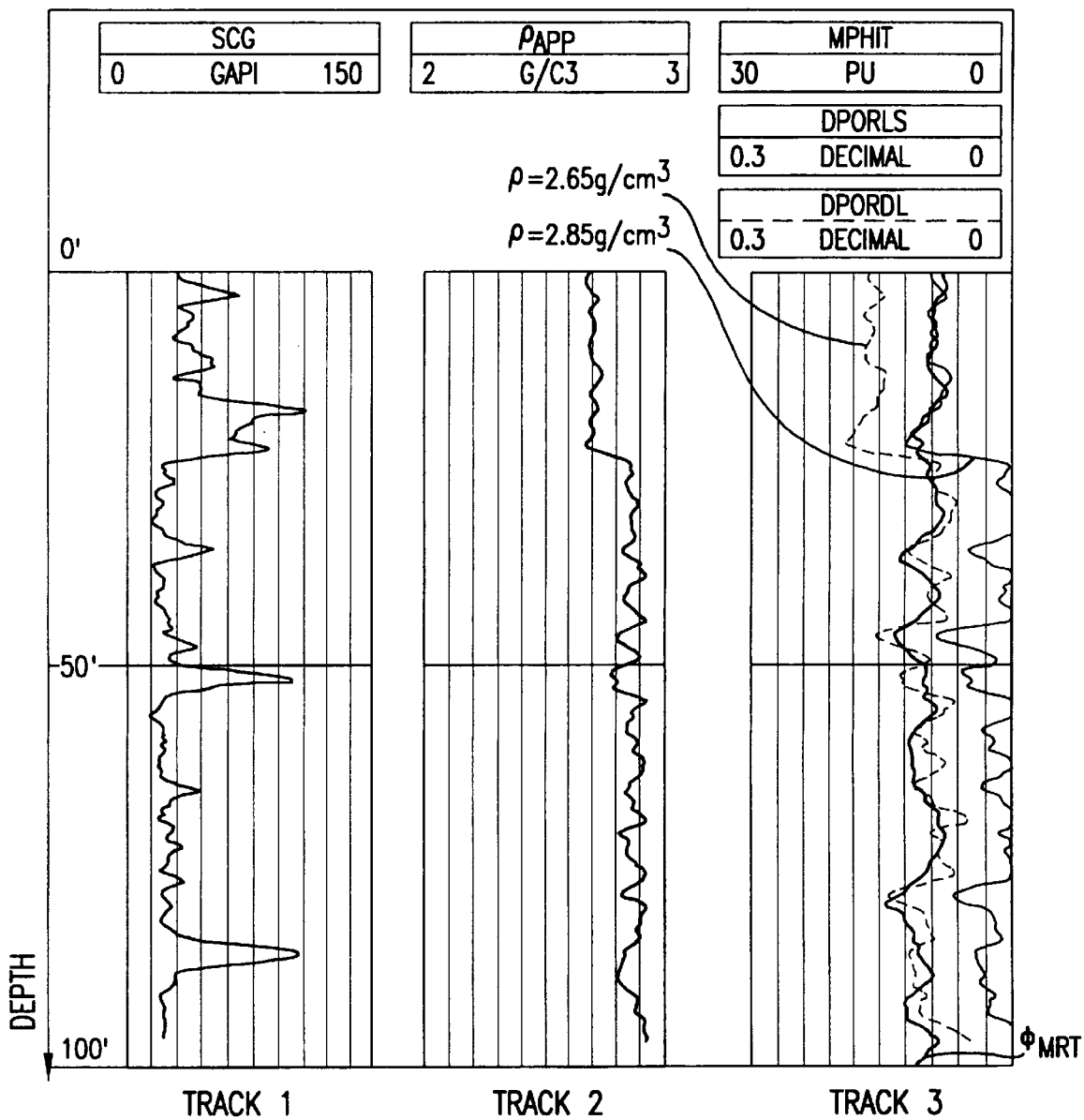
FIG. 13 illustrates the lithology-independent nature of the total porosity $\Phi_{MRT}$ measured in accordance with the present invention.

The result of this calculation is shown in FIG. 13. At X623 ft, an abrupt change in lithology exists from an apparent matrix density of ~2.68 g/cm$^3$ to ~2.85 g/cm$^3$. From core analysis, it is known that the sandstone above X623 consists mostly of quartz (2.657 g/cm$^3$) and that the limestone/dolomite mix below X623 is mostly dolomite (2.85 g/cm$^3$). Track 3 shows density porosites for $\rho=2.65$ g/cm$^3$ (dashed line), and for $\rho=2.85$ g/cm$^3$ (solid line), to be in excellent agreement with the MRIL porosity $\Phi_{MRT}$ (bold solid line). In mixed or unknown and gas-free formations, the NMR measurement can provide a stand-alone porosity answer that is independent of core analysis, and/or crossplot techniques that rely on different tool responses.

Figure 14:
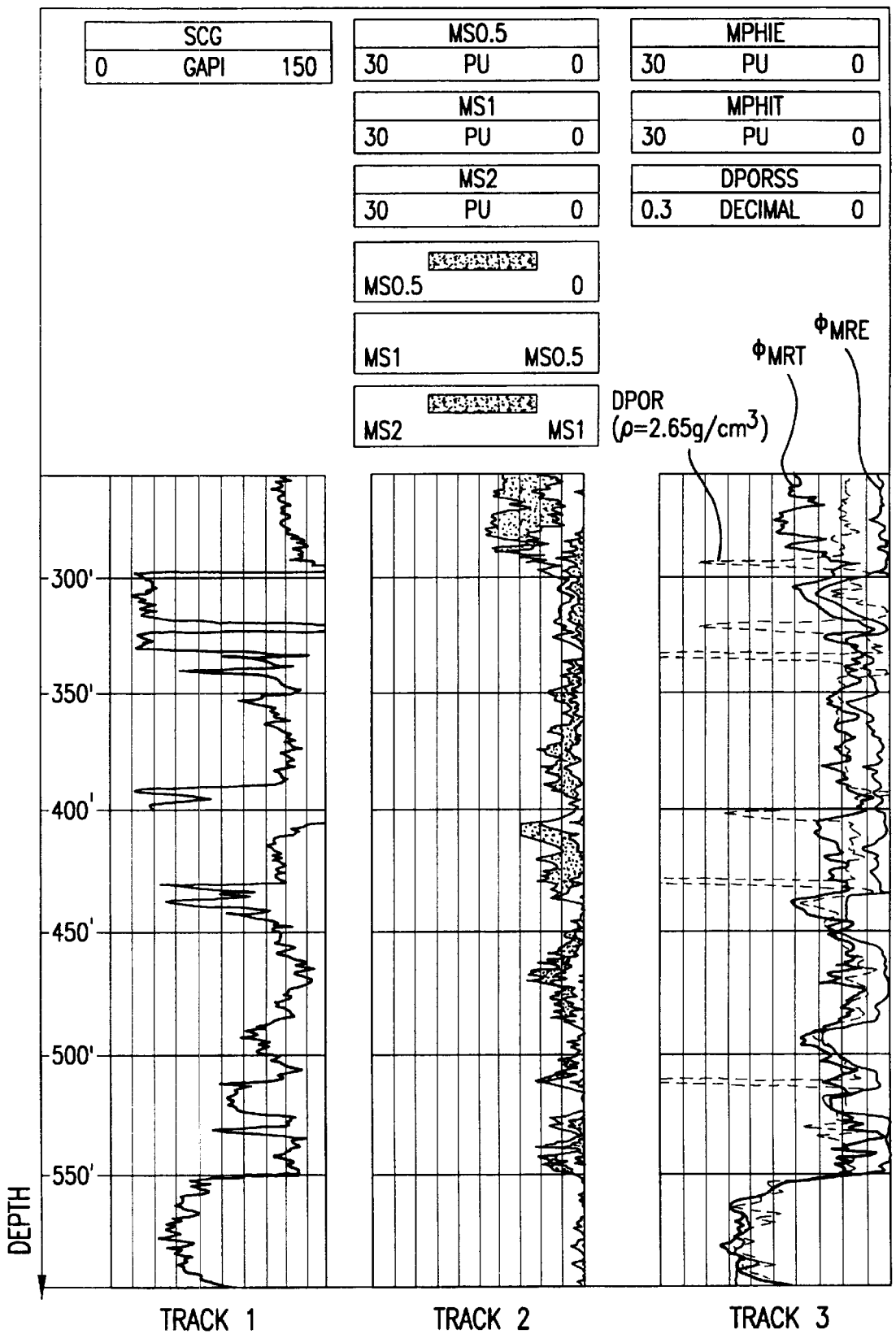
FIG. 14 illustrates the behavior of very fast relaxation components measured in various lithologies in accordance with the method of the present invention.

FIG. 14 illustrates the behavior of the very fast relaxation components computed in accordance with the present invention in various lithologies. Track 1 is the spectral gamma ray in API units 1–150, and track 3 contains porosites on a scale of 0 to 0.3. Density porosity calibrated for a sandstone matrix ($\rho=2.65$ g/cm$^3$) is shown dashed; effective MRIL porosity is light solid; total MRIL porosity is shown in bold solid. Evidently, the density log is affected by hole rugosity in several places, whereas the MRIL is not (for example, at X295, X322, X334, X402, X431 and X52). In track 2, the difference $\Phi_{MRT} - \Phi_{MRE}$ is broken down into the fastest three $T_2$ relaxation components. The individual bands in track 2 indicate the individual intensities of the relaxation modes: 2 ms (left, black), 1 ms (center, white) and 0.5 ms (right, black). The sandstone sections (X340–X390 and X418–X595) show good agreement between the density log and $\Phi_{MRT}$. In the very clean section from X555 to X595, no clay-bound signal is detected (track 2), and full agreement exists between density porosity, $\Phi_{MRE}$ and $\Phi_{MRT}$. In the shaly sections (high gamma ray readings) a characteristic clay-bound water signal develops with a $T_2$ of 1–2 ms. Density porosity and $\Phi_{MRT}$ continue to agree, while effective porosity is considerably reduced and at places vanishes. Differences between density porosity and total MRIL porosity, where MRIL porosity is higher than density porosity, are indicative of lithologies with matrix densities greater than 2.65 g/cm$^3$. This is the case in the top shale (above X281), where recomputing the density response yields an apparent matrix density close to 2.80 g/cm$^3$. The clay-bound signal has a clear signature of 1–2 ms. Below the shale section, in the interval X281–X330, layers of limestone and shale are interspersed. For example, the limestone at X310 is identified by high effective porosity and an undercall in sandstone density porosity. The 1–2 ms $T_2$ signature is missing in this section, replaced by a very fast decay below 1 ms, which could be due to microporosity in the limestone or due to interbedded, dense shale thinner than the logging tools' resolution limits.

OTHER APPLICATIONS

The novel pulse sequence and processing method was described above with reference to NMR logging. However, the sequence and method are equally applicable in various other situations, including NMR measurements of porous materials. For example, U.S. Pat. No. 5,672,968, one of the co-inventors of which is the inventor of the present application, describes analysis of cement-based materials using NMR measurements. The content of this application is herewith expressly incorporated for all purposes.

As shown in the U.S. Pat. No. 5,672,968, concrete which is used for construction can be analyzed to determine its structural properties, such as strength, potential for shrinkage and others in the final cured concrete. As the concrete is a mixture of various materials and includes a water portion, the method of the present invention can be used to determine various attributes of the materials, such as the curing properties of the various cement mixtures.

It should be clear to those skilled in the art that the pulse sequence and the method of the present invention can also be used in measuring properties of samples of porous materials in a laboratory setting, as well as in situ logging-type including logging/measuring while drilling (LWD/MWD) measurements, as described in detail above.

NOMENCLATURE $\Phi_{MRE}$ magnetic resonance effective porosity
$\Phi_{MRT}$ magnetic resonance total porosity
$\rho_b$ bulk density
$\rho_{app}$ apparent matrix density
$\rho_{fl}$ fluid density
$\rho_{ma}$ matrix density
$N_e$ number of echoes in a single echo train
$T_1$ magnetic resonance longitudinal relaxation time
$T_2$ magnetic resonance transversal relaxation time
$T_e$ echo-to-echo sampling time
$T_{pr}$ partial recovery time
$T_w$ wait time Although the present invention has been described in connection with a preferred embodiment, it is not intended to be limited to the specific form set forth herein, but is intended to cover such modifications, alternatives, and equivalents as can be reasonably included within the spirit and scope of the invention as defined by the following claims.

TABLE 1

STATIONARY MEASUREMENTS

| Data set | Depth | Echo Spacings | Recovery Times | Comments |
| --- | --- | --- | --- | --- |
| S1120SF | 1120 | 1.2 + 0.51 | 3000 ms | standard |
| S1120TRX | 1120 | 0.51 | 3000 + 10 + 20 + 50 | special fast recovery |
| S1122TRX | 1122 | 1.2 + 0.51 | 3000 | standard |
| S1122XXX | 1122 | 0.51 | 3000 + 10 + 20 + 50 | special fast recovery |
| S11124SF | 1124 | 1.2 + 0.51 | 3000 | standard |
| S1124TRX | 1124 | 0.51 | 3000 + 10 + 20 + 50 | special fast recovery |
| S1131SF | 1131 | 1.2 + 0.51 | 3000 | standard |
| S1131TRX | 1131 | 0.51 | 3000 + 10 + 20 + 50 | special fast recovery |
| S1150SF | 1150 | 1.2 + 0.51 | 3000 | standard |
| S1150TRX | 1150 | 0.51 | 3000 + 10 + 20 + 50 | special fast recovery |
| S1157SF | 1157 | 1.2 + 0.51 | 3000 | standard |
| S1157TRX | 1157 | 0.51 | 3000 + 10 + 20 + 50 | special fast recovery |

TABLE 2

LOGGING MEASUREMENTS

| Data set | Echo Spacing | Recovery Times | Comments |
|---|---|---|---|
| T1MAGM | 1.2 ms | $T_w$ = 3000 ms | standard log |
| T1MAGR | 1.2 | $T_w$ = 3000 | same as T1MAGM |
| T2MAGM | 0.6 | $T_w$ = 3000 | standard log |
| T2MAGR | 0.6 | $T_w$ = 3000 | same as T1MAGM |
| T3MAGM | 0.51 | $T_w$ = 3000 | standard log |
| T3MAGR | 0.51 | $T_w$ = 3000 | same as T1MAGM |
| T9M | 0.51 | $T_w$ = 3000, $T_3$ = 10 | 51 bursts of 16 echoes each |
| T9R | 0.51 | $T_w$ = 3000, $T_3$ = 10 | same as T9M |
| T10M | 0.51 | $T_w$ = 3000, $T_3$ = 50 | 51 bursts of 16 echoes each |
| T10R | 0.51 | $T_w$ = 3000, $T_3$ = 50 | same as T10M |
| T20M | 0.51 | $T_w$ = 3000, $T_3$ = 50 | 51 bursts of 16 echoes each |
| T21M | 0.51 | $T_w$ = 3000, $T_3$ = 100 | 51 bursts of 16 echoes each |

TABLE 3

CLAY TYPES AND PROPERTIES OF SAMPLES

| Clay Types | Clay ID | Total Surface Area ($m^2$/g) | CEC (meq/100 g) | Remarks |
|---|---|---|---|---|
| montmorillonite | SWy-2 | 760 (theoretical[a]) 616 (measured[a]) | 76[b] | |
| illite | 1Mt-1 | 93 (measured[a]) | 15[c] | <10% smectite layers |
| kaolinite | KGa-1b | 18 (measured[a]) | 2[b] | |
| chlorite | CCa-2 | 40 (estimated[d]) | n/a | sample contains large amount of iron |

All samples were obtained from the Clay Mineral Society, Source Clay Minerals Repository, Univ. of Missouri, Columbia, MO.
[a]) Unpublished data, courtesy of D. Mardon (eGME adsorption measurements).
[b]) van Olphen and Fripiat, 1979.[12]
[c]) Hower and Mowatt, 1966.[13]
[d]) Ellis, 1987.[5]

TABLE 4

RESULTS OF LABORATORY $T_2$ MEASUREMENTS

| Clay ID | Water Weight per dry clay weight (%) | NMR Visibility at Te = 0.5 ms (ms) | $T_2$ of clay-bound water at Te – 0.5 ms (ms) | Apparent $\rho_2$ surface relaxivity ($\mu$m/s) | Remarks |
|---|---|---|---|---|---|
| SWy-2 | 7.0 | 20 | — | — | $T_2$ < 0.2 ms |
| | 18.9 | 90 | 0.3 | 1 | |
| | 31.1 | 100 | 0.5 | 1 | |
| | 54.4 | 100 | 1 | 0.9 | $T_1$ = 1.5 ms |
| 1Mt-1 | 8.8 | 90 | 1 | 0.9 | |
| | 15.8 | 100 | 2 | 0.8 | |
| KGa-1b | 11.7 | 100 | 8 | 0.8 | |
| | 17.4 | 100 | 12 | 0.8 | |
| | 20.0 | 100 | 16 | 0.7 | $T_1$ = 30 ms |
| CCa-2 | 7.5 | 100 | 5 | 0.4 | $\rho_2$ may be too low due to over estimated surface area |

Measurements were made at 1 MHz and at 25° C. on the clay samples listed in Table 1. Samples were saturated with different amounts of brine, pressed at 2500 psi and sealed. Water weight was determined from weight loss by overnight drying in a vacuum chamber at 103° C. NMR visibility is the ratio of calibrated NMR amplitude (in ml of water) per ml of water content determined from weight loss. Apparent transversal surface relaxivities $\rho_2$ were calculated from specific surface areas (Table 1), the water-to-dry weight ratios and from $T_2$'s.

What is claimed is:
1. A nuclear magnetic resonance (NMR) method for measuring an indication of attributes of materials containing a fluid state, the method comprising the steps of:
 (a) applying in a pre-determined sequence at least two short NMR pulse trains, each pulse train comprising at least one pulse and resulting in at least one response signal from said materials, the interval $T_s$ between any two short pulse trains being less than the time required for polarization of substantially all nuclear magnetization in bulk fluids of the fluid state contained in said materials;
 (b) stacking NMR response signals from said at least two short NMR pulse trains to obtain time domain data indicative of fast decay components of the fluid state contained in said materials;

(c) combining said at least two short NMR pulse trains with one or more regular NMR pulse-echo trains, wherein a regular NMR pulse train is preceded by a recovery time $T_w$ sufficient to substantially polarize all nuclear magnetization in the fluid state and the duration of each of said one or more regular NMR pulse trains is longer than the duration of each of said short NMR pulse trains; and (d) determining overall relaxation properties of the fluid state contained in said materials from the combination of said at least two short NMR pulse trains with said one or more regular NMR pulse-echo trains.

2. The method of claim 1 wherein the duration of each of said at least two short NMR pulse trains is less than the time required for signal decay of substantially all nuclear magnetization resonance from bulk fluid of the fluid state in said materials.

3. The method of claim 2 wherein said at least two short NMR pulse trains are Carr-Purcell-Meiboom-Gill (CPMG) pulse-echo trains.

4. The method of claim 2 wherein said at least two short NMR pulse trains are pulse/free-induction-decay (FID) trains.

5. The method of claim 1 further comprising the steps of converting the time domain data into $T_2$ spectrum data; and determining attributes of said materials from the $T_2$ spectrum data.

6. The method of claim 1 further comprising the step of converting time domain data obtained from (i) said stacked short NMR pulse trains and (ii) from said regular pulse-echo trains into combined $T_2$ spectrum data; and extracting information about attributes of said materials from said combined $T_2$ spectrum data.

7. The method of claim 6 wherein said attributes of said materials comprises the total magnetic resonance porosity $\Phi_{MRT}$ of said materials which is computed as:

$$\Phi_{MRT} = \Phi_{MRE} + \Phi_B$$

where:

$\Phi_{MRE}$ is the magnetic resonance effective porosity derived from components in the combined $T_2$ spectrum that correspond to said regular pulse NMR trains, and $\Phi_B$ is the bound porosity derived from components in the combined $T_2$ spectrum that correspond to said stacked short NMR pulse trains.

8. The method of claim 1 wherein said short NMR pulse trains and said regular NMR pulse trains are applied in a single measurement of said materials.

9. The method of claim 1 wherein said short NMR pulse trains and said regular NMR pulse trains are applied in separate measurements of said materials.

10. The method of claim 1 further comprising the steps of obtaining time domain data corresponding to response signals from said one or more regular NMR pulse trains;

combining time domain data obtained from (i) said stacked short NMR pulse trains and (ii) from said regular NMR pulse trains; and extracting information about attributes of said materials from said combined data.

11. The method of claim 1 further comprising the step of deriving a measure of shale volume from the $T_2$ spectrum data.

12. The method of claim 11 further comprising the step of deriving a measure of the net-to-gross ratio of a rock formation from the measure of shale volume.

13. The method of claim 1 wherein said at least two short NMR pulse trains are applied to depth of investigation in the borehole which is shallow compared with the depth of investigation in the borehole for said regular CPMG pulse-echo measurements of said earth formation.

14. The method of claim 13 further comprising the steps of converting time domain data obtained from (i) said stacked short NMR pulse trains and (ii) from said regular CPMG measurements into combined $T_2$ spectrum data; and extracting information about attributes of said earth formation from said combined $T_2$ spectrum data, wherein the difference in the depth of investigation in (i) and (ii) is used to estimate the true movable fluid contents of the earth formation.

15. The method of claim 1 further comprising the steps of obtaining time domain data corresponding to response signals from said one or more regular NMR pulse trains; combining time domain data obtained from (i) said stacked short NMR pulse trains and (ii) from said regular CPMG trains; and extracting information about attributes of said earth formation from said combined data.

16. An NMR borehole logging method for measuring an indication of petrophysical attributes of an earth formation, the method comprising the steps of:

(a) applying in a pre-determined sequence at least two short NMR pulse trains, each pulse train comprising at least one pulse and resulting in at least one response signal from said earth formation, the interval $T_s$ between any two short pulse trains being less than the time required for polarization of substantially all nuclear magnetization in any bulk fluid contained in said earth formation; and (b) stacking NMR response signals from said at least two short NMR pulse trains to obtain time domain data indicative of fast decay components of a fluid state contained in said earth formation;

(c) combining said at least two short NMR pulse trains with regular Carr-Purcell-Meiboom-Gill (CPMG) pulse-echo measurements of said earth formation, wherein a regular CPMG pulse-echo train is preceded by a recovery time $T_w$ sufficient to substantially polarize all nuclear magnetization in the fluid state; and (d) determining overall relaxation properties of the fluid state contained in said earth formation from the combination of said least two short NMR pulse trains with said regular CPMG pulse-echo measurements.

17. The method of claim 16 wherein the duration of each of said at least two short NMR pulse trains is less than the time required for signal decay of substantially all nuclear magnetization resonance from bulk fluid of the fluid state contained in said earth formation.

18. The method of claim 17 wherein said at least two short NMR pulse trains are Carr-Purcell-Meiboom-Gill (CPMG) pulse-echo trains.

19. The method of claim 17 wherein said at least two short NMR pulse trains are pulse/free-induction-decay (FID) trains.

20. The method of claim 17 further comprising the step of identifying a portion of the $T_2$ spectrum as corresponding to very heavy crude hydrocarbons, such as bitumen.

21. The method of claim 17 further comprising the step of identifying a portion of the $T_2$ spectrum as corresponding to clay-bound fluids.

22. The method of claim 17 wherein an indication of petrophysical attributes of the earth formation is provided by interpreting external resistivity measurements data in view of the portion of the $T_2$ spectrum identified as corresponding to clay-bound fluids.

23. The method of claim 16 further comprising the steps of converting the time domain data into $T_2$ spectrum data; and determining attributes of said earth formation from the $T_2$ spectrum data.

24. The method of claim 23 wherein an indication of petrophysical attributes of the earth formation is provided by associating increasing cation exchange capacitance (CEC) values to porosity components with decreasing $T_2$ relaxation values in the T2 spectrum.

25. The method of claim 16 further comprising the step of converting time domain data obtained from (i) said stacked short NMR pulse trains and (ii) from said regular pulse-echo measurements into combined $T_2$ spectrum data; and extracting information about attributes of said earth formation from said combined $T_2$ spectrum data.

26. The method of claim 25 wherein the petrophysical attributes of the earth formation comprises the clay minerals content which is determined on the basis of components of the $T_2$ spectrum.

27. The method of claim 25 wherein said attributes of said earth formation comprises the total magnetic resonance porosity $\Phi_{MRT}$ of said materials which is computed as:

$$\Phi_{MRT} = \Phi_{MRE} + \Phi_{CIB}$$

where:

$\Phi_{MRE}$ is the magnetic resonance effective porosity derived from components in the combined $T_2$ spectrum that correspond to said regular pulse-echo measurements, and $\Phi_{CIB}$ is the bound porosity derived from components in the combined $T_2$ spectrum that correspond to said stacked short NMR pulse trains.

28. The method of claim 27 further comprising the step of combining the magnetic resonance total porosity $\Phi_{MRT}$ with an external measure of the total porosity $\Phi_T$ to derive additional information about petrophysical attributes of the earth formation, such additional information comprising an estimate of the presence of gas in the earth formation.

29. The method of claim 27 further comprising the step of combining the magnetic resonance total porosity $\Phi_{MRT}$ with an external measure of the total porosity $\Phi_T$ to derive additional information about petrophysical attributes of the earth formation, such additional information comprising an estimate of the saturations of oil and gas in the earth formation.

30. The method of claim 27 further comprising the step of combining the magnetic resonance total porosity $\Phi_{MRT}$ with porosity measurements on core samples of similar rock formations and deriving petrophysical information from said combination.

31. The method of claim 16 wherein said short NMR pulse trains and said regular CPMG trains are applied in a single pass through the borehole.

32. The method of claim 16 wherein said short NMR pulse trains and said regular CPMG trains are applied in separate passes through the borehole.

33. The method of claim 16 further comprising the step of identifying a portion of the fast $T_2$ spectrum as fluids bound to clays susceptible to swelling, such as smectites and illites.

34. The method of claim 16 further comprising the step of combining short CPMG trains with CPMG trains with reduced recovery time sufficient to polarize substantially all nuclear magnetization from fluids in a bound state and insufficient to polarize all nuclear magnetization from fluids in an unbound fluid state of the earth formation.

35. The method of claim 34 wherein said short CPMG trains and said CPMG trains with reduced recovery time are applied in a single pass through the borehole.

36. The method of claim 34 wherein said short CPMG trains and said CPMG trains with reduced recovery time are applied in separate passes through the borehole.

37. The method of claim 34 wherein the petrophysical attributes of the earth formation comprises the total bound fluid porosity $\Phi_{BT}$ of the earth formation computed as:

$$\Phi_{BT} = \Phi_{CIB} + \Phi_{CapB}$$

where $\Phi_{CIB}$ is the clay bound porosity determined from said short CPMG trains, and $\Phi_{CapB}$ is the capillary bound porosity determined from said CPMG trains with reduced recovery time.

38. The method of claim 37 further comprising the step of deriving the free-fluid porosity $\Phi_{FF}$ of the earth formation using the expression:

$$\Phi_{FF} = \Phi_T - \Phi_{BT}$$

where $\Phi_T$ is an external measure of the total porosity.

39. The method of claim 16 wherein parameters of said at least two short NMR trains are adjustable.

40. The method of claim 16 further comprising the step of processing said time domain data to obtain a measure of the pore pressure in said earth formation.

41. The method of claim 16 further comprising the step of processing said time domain data and combining said processed data with an external measure of bulk density to obtain additional information about the petrophysical attributes of said earth formation.

42. The method of claim 41 wherein said additional information is the apparent matrix density $\rho_{app}$ computed according to the following formula:

$$\rho_{app} = \frac{\rho_b - \phi_{MRT}}{1 - \phi_{MRT}}$$

where $\rho_b$ is the bulk density, and $\Phi_{MRT}$ is the total porosity in decimal units.

43. A nuclear magnetic resonance (NMR) method for measuring an indication of attributes of materials containing a fluid state, the method comprising the steps of:

(a) applying in a pre-determined sequence at least two short NMR pulse trains, each pulse train comprising at least one pulse and resulting in at least one response signal from said materials, the interval $T_s$ between any two short pulse trains being less than the time required for polarization of substantially all nuclear magnetization in bulk fluids of the fluid state contained in said materials; and (b) stacking NMR response signals from said at least two short NMR pulse trains to obtain time domain data indicative of fast decay components of the fluid state contained in said materials, wherein said attributes of materials containing a fluid state comprise the curing properties of cement mixtures.

44. The method of claim 43 wherein the cement mixtures comprise concrete.

45. The method of claim 43 wherein the cement mixtures comprise concrete which is used for construction, and the curing properties comprise structural properties of the cured concrete, such as strength and potential for shrinkage.

46. An NMR method for measuring an indication of an attribute of a volume of earth formation in a borehole, comprising the steps of:
  a) applying oscillating magnetic fields according to a pre-specified pulse sequence, said pulse sequence comprising: a regular Carr-Purcell-Meiboom-Gill (CPMG) train having between about 100 and 10,000 echoes, followed by at least one short wait interval $T_s$ of approximately 10–100 ms duration, followed next by at least one short CPMG train having between about 1 and 100 echoes;
  b) measuring NMR signals representing spin-echo relaxation of a population of particles in the geologic structure; and
  c) processing NMR signals corresponding to said regular CPMG train and NMR signals corresponding to said at least one short CPMG train to determine values for the magnetic resonance effective porosity ($\Phi_{MRE}$) of the volume of the earth formation and values for the clay-bound porosity $\Phi_{CIB}$ of the volume of the earth formation.

* * * * *